United States Patent
Freeman et al.

(10) Patent No.: US 12,226,645 B2
(45) Date of Patent: *Feb. 18, 2025

(54) MEDICAL DEVICE OPERATIONAL MODES

(71) Applicant: ZOLL Medical Corporation, Chelmsford, MA (US)

(72) Inventors: Gary A. Freeman, Waltham, MA (US); Thomas E. Kaib, Irwin, PA (US); Shane S. Volpe, Saltsburg, PA (US)

(73) Assignee: ZOLL Medical Corporation, Chelmsford, MA (US)

(*) Notice: Subject to any disclaimer, the term of this patent is extended or adjusted under 35 U.S.C. 154(b) by 60 days.

This patent is subject to a terminal disclaimer.

(21) Appl. No.: 18/053,613

(22) Filed: Nov. 8, 2022

(65) Prior Publication Data

US 2023/0066047 A1 Mar. 2, 2023

Related U.S. Application Data

(63) Continuation of application No. 16/693,769, filed on Nov. 25, 2019, now Pat. No. 11,529,527, which is a
(Continued)

(51) Int. Cl.
*A61N 1/39* (2006.01)
*A61B 5/00* (2006.01)
(Continued)

(52) U.S. Cl.
CPC ........ *A61N 1/3987* (2013.01); *A61B 5/02438* (2013.01); *A61B 5/361* (2021.01);
(Continued)

(58) Field of Classification Search
CPC .. A61N 1/0484; A61N 1/3904; A61N 1/3625; A61N 1/3925; A61N 1/3931
See application file for complete search history.

(56) References Cited

U.S. PATENT DOCUMENTS 5,944,669 A 8/1999 Kaib
10,532,217 B2 * 1/2020 Freeman .............. A61N 1/3925
(Continued)

FOREIGN PATENT DOCUMENTS

EP 2420185 A2 2/2012
WO 20150123198 8/2015

OTHER PUBLICATIONS

Partial Supplementary European Search Report for European Patent Application 16852304.1, dated Apr. 2, 2019, 8 pages.
(Continued)

*Primary Examiner* — George R Evanisko
(74) *Attorney, Agent, or Firm* — Finch & Maloney PLLC

(57) ABSTRACT

An ambulatory medical device comprising: a monitoring component comprising at least one sensing electrode for detecting a cardiac condition of a patient; at least one processor configured for: adjusting one or more detection parameters for detecting the cardiac condition of the patient based at least in part on at least one of 1) one or more environmental conditions and 2) input received from the monitoring component; and providing at least one of an alarm and a treatment in response to detecting the cardiac condition of the patient based on the adjusted one or more detection parameters.

20 Claims, 14 Drawing Sheets

Related U.S. Application Data continuation of application No. 15/265,973, filed on Sep. 15, 2016, now Pat. No. 10,532,217.

(60) Provisional application No. 62/235,165, filed on Sep. 30, 2015.

(51) Int. Cl.
*A61B 5/024* (2006.01)
*A61B 5/361* (2021.01)
*A61N 1/04* (2006.01)
*A61N 1/362* (2006.01)
*A61B 5/0205* (2006.01)
*A61B 5/11* (2006.01)

(52) U.S. Cl.
CPC ............ *A61B 5/4809* (2013.01); *A61B 5/746* (2013.01); *A61N 1/046* (2013.01); *A61N 1/0484* (2013.01); *A61N 1/3625* (2013.01); *A61N 1/3925* (2013.01); *A61B 5/0205* (2013.01); *A61B 5/02055* (2013.01); *A61B 5/1112* (2013.01); *A61B 5/1118* (2013.01); *A61B 5/4836* (2013.01); *A61B 5/6805* (2013.01); *A61B 5/6831* (2013.01); *A61B 2560/0242* (2013.01)

(56) References Cited

U.S. PATENT DOCUMENTS

| | | |
|---|---|---|
| 2003/0211678 A1 | 11/2003 | Michael |
| 2005/0124864 A1 | 6/2005 | Mack et al. |
| 2008/0306560 A1 | 12/2008 | Macho et al. |
| 2010/0241181 A1 | 9/2010 | Savage et al. |
| 2010/0286532 A1 | 11/2010 | Farringdon et al. |
| 2013/0231711 A1 | 9/2013 | Kaib |
| 2014/0046391 A1 | 2/2014 | Cowan et al. |
| 2014/0236029 A1 | 8/2014 | Averina et al. |
| 2014/0276119 A1 | 9/2014 | Venkatraman et al. |
| 2014/0324112 A1 | 10/2014 | Macho et al. |
| 2014/0365142 A1 | 12/2014 | Baldwin |
| 2015/0039053 A1 | 2/2015 | Kaib et al. |
| 2016/0074667 A1 | 3/2016 | Sullivan et al. |

OTHER PUBLICATIONS

Supplementary European Search Report for European Patent Application 16852304.1, dated Sep. 2, 2019, 13 pages.
International Search Report and Written Opinion for PCT Application No. PCT/US2016/051833, dated Dec. 1, 2016, 12 pages.
Summons to attend oral proceedings pursuant to Rule 115(1) EPC mailed Jun. 22, 2023 for European Patent Office Application 16 852 304.1, 10 pages.
Extended Europe Search Report for Europe Patent Application 24182679.1, dated Sep. 16, 2024 (9 pages).

* cited by examiner

MEDICAL DEVICE OPERATIONAL MODES

This application is a continuation of U.S. application Ser. No. 16/693,769, filed Nov. 25, 2019 and published as U.S. Patent Application Publication No. 20200188682, which is a continuation of U.S. application Ser. No. 15/265,973, filed Sep. 15, 2016, now U.S. Pat. No. 10,532,217, and published as U.S. Patent Application Publication No. 20170087371, which claims priority under 35 USC § 119(e) to U.S. Patent Application Ser. No. 62/235,165, filed on Sep. 30, 2015. The disclosures of each of the foregoing applications are incorporated herein by reference in their entirety.

BACKGROUND

This disclosure relates to systems and techniques for changing operational parameters and modes of a medical device.

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

For example, certain medical devices operate by substantially continuously monitoring the patient's heart through one or more sensing electrodes for treatable arrhythmias and, when such is detected, the device applies corrective electrical pulses directly to the heart through one or more therapy electrodes.

SUMMARY

In one aspect, an ambulatory medical device includes a monitoring component that includes at least one sensing electrode for detecting a cardiac condition of a patient. The ambulatory medical device also includes at least one processor. The at least one processor is configured for adjusting one or more detection parameters for detecting the cardiac condition of the patient based at least in part on at least one of 1) one or more environmental conditions and 2) input received from the monitoring component. The at least one processor is also configured for providing at least one of an alarm and a treatment in response to detecting the cardiac condition of the patient based on the adjusted one or more detection parameters.

Implementations can include one or more of the following features.

In some implementations, the adjusting includes dynamically adjusting the detection parameters for detecting the cardiac condition.

In some implementations, the ambulatory medical device includes a sensor. The at least one processor is configured to sense the one or more environmental conditions based on input from the sensor.

In some implementations, the sensor includes a moisture sensor.

In some implementations, the sensor includes a motion sensor.

In some implementations, the sensor includes a pressure sensor. The at least one processor is configured to monitor a patient sleep while the patient is asleep. The pressure sensor detects a pressure indicative of the patient sitting or lying down.

In some implementations, the one or more environmental conditions include a location of the ambulatory medical device.

In some implementations, the ambulatory medical device includes a location module configured to determine the location of the ambulatory medical device.

In some implementations, the location module is one of a GPS module, an NFC module, a Bluetooth® module, and a WLAN module.

In some implementations, the ambulatory medical device includes an audio interface configured to receive and provide audible information.

In some implementations, the at least one processor is configured to adjust the operational parameters based at least in part on the received audible information.

In some implementations, the audio interface is configured to interact with an audio system that receives, provides, or receives and provides the audible information.

In some implementations, the ambulatory medical device includes at least one therapy electrode in communication with the at least one processor.

In some implementations, the at least one therapy electrode is configured to deliver defibrillation current.

In some implementations, the at least one therapy electrode is configured to deliver one or more pacing pulses.

In some implementations, the at least one processor is configured for detecting that the cardiac condition may be occurring. The detecting is based at least in part on 1) input received from the monitoring component and 2) one or more detection parameters that correspond to the adjusted detection parameters. The at least one processor is also configured for selecting a treatment sequence corresponding to the cardiac condition.

In some implementations, the monitoring component is configured to monitor one or more patient parameters. The one or more patient parameters include one or more of a heart rate, a respiration rate, a blood pressure, and one or more occurrences of pre-ventricle contraction (PVC).

In some implementations, the one or more adjusted detection parameters include a lower sensitivity level for detecting the cardiac condition than a sensitivity level of the detection parameters prior to the adjusting.

In some implementations, the one or more adjusted detection parameters include a higher sensitivity level for detecting the cardiac condition than a sensitivity level of the detection parameters prior to the adjusting.

In some implementations, the sensitivity level is based at least in part on motion detected by a motion sensor of the ambulatory medical device.

In some implementations, the sensitivity level is inversely proportional to an intensity of the motion detected by the motion sensor.

In some implementations, the cardiac condition is an arrhythmia condition.

In another aspect, an ambulatory medical device includes a monitoring component that includes at least one sensing electrode for detecting a cardiac condition of a patient. The ambulatory medical device also includes at least one processor configured for adjusting one or more treatment parameters for treating the cardiac condition of the patient based at least in part on one or more environmental conditions. The at least one processor is also configured for providing at least one of an alarm and a treatment in response to detecting the cardiac condition of the patient based on the adjusted one or more treatment parameters.

Implementations can include one or more of the following features.

In some implementations, the cardiac condition is an arrhythmia condition.

In some implementations, the ambulatory medical device includes a wearable medical device.

In some implementations, the ambulatory medical device includes a garment configured to be worn about a torso of the patient.

In another aspect, an ambulatory medical device includes a monitoring component that includes at least one sensing electrode for detecting a cardiac condition of a patient. The ambulatory medical device also includes at least one processor configured for selecting an operating mode of the ambulatory medical device based at least in part on at least one of 1) one or more environmental conditions and 2) input received from the monitoring component. The mode corresponds to a state of the patient monitored by the ambulatory medical device.

Implementations can include one or more of the following features.

In some implementations, the operating mode is selected based on an input received via a user interface of the ambulatory medical device.

In some implementations, the ambulatory medical device includes a sensor. The at least one processor is configured to detect the one or more environmental conditions based on input from the sensor.

In some implementations, the sensor includes a moisture sensor. The at least one processor is configured to select a water operating mode if the moisture sensor detects a moisture content that meets or exceeds a threshold.

In some implementations, the sensor includes a motion sensor. The at least one processor is configured to select an activity operating mode if the motion sensor detects a motion indicative of the patient being in an active state.

In some implementations, the sensor includes a pressure sensor. The at least one processor is configured to select a patient sleep operating mode if the pressure sensor detects a pressure indicative of the patient sitting or lying down.

In some implementations, the one or more environmental conditions include a location of the ambulatory medical device.

In some implementations, the ambulatory medical device includes a location module configured to determine the location of the ambulatory medical device.

In some implementations, the location module is one of a GPS module, an NFC module, a Bluetooth® module, and a WLAN module.

In some implementations, the ambulatory medical device includes an audio interface configured to receive and provide audible information.

In some implementations, the at least one processor is configured to select the operating mode based at least in part on the received audible information.

In some implementations, the audio interface is configured to interact with an audio system that receives, provides, or receives and provides the audible information.

In some implementations, the audio system is a car audio system.

In some implementations, the at least one processor is configured to select the operating mode based at least in part on 1) the one or more environmental conditions and 2) the input received from the monitoring component.

In some implementations, the ambulatory medical device includes at least one therapy electrode in communication with the at least one processor.

In some implementations, the at least one therapy electrode is configured to deliver defibrillation current.

In some implementations, the at least one therapy electrode is configured to deliver one or more pacing pulses.

In some implementations, the at least one processor is configured for detecting that the cardiac condition may be occurring. The detecting is based at least in part on 1) input received from the monitoring component and 2) one or more detection parameters that correspond to the selected operating mode. The at least one processor is also configured for selecting a treatment sequence corresponding to the cardiac condition. The treatment sequence is associated with the selected operating mode.

In some implementations, the one or more detection parameters include an extended amount of time in which the at least one processor detects that the cardiac condition may be occurring that is longer than an amount of time in a default operating mode.

In some implementations, the one or more detection parameters include a reduced amount of time in which the at least one processor detects that the cardiac condition may be occurring that is shorter than an amount of time in a default operating mode.

In some implementations, the monitoring component is configured to monitor one or more patient parameters. The one or more patient parameters include one or more of a heart rate, a respiration rate, a blood pressure, and one or more occurrences of pre-ventricle contraction (PVC).

In some implementations, a motor vehicle operating mode is among the modes from which the at least one processor is configured to select.

In some implementations, the at least one processor is configured for providing an indication that the patient should refrain from operating a motor vehicle based at least in part on one or more of the patient parameters monitored by the monitoring component.

In some implementations, the one or more detection parameters include a lower sensitivity level for detecting the cardiac condition than a sensitivity level in a default operating mode.

In some implementations, the one or more detection parameters include a higher sensitivity level for detecting the cardiac condition than a sensitivity level in a default operating mode.

In some implementations, the higher sensitivity level is based at least in part on motion detected by a motion sensor of the ambulatory medical device.

In some implementations, the higher sensitivity level is inversely proportional to an intensity of the motion detected by the motion sensor.

In some implementations, the selected treatment sequence includes an extended amount of time in which a response is expected from the patient that is longer than an amount of time in a default operating mode.

In some implementations, the at least one processor is configured for carrying out the treatment sequence. The treatment sequence includes causing at least one therapy electrode to deliver a therapy to the patient.

In some implementations, the treatment sequence includes providing an indication that the therapy is about to be delivered to the patient.

In some implementations, the indication is an audible alarm. A volume of the alarm is based on the selected operating mode.

In some implementations, the at least one processor is configured to, before causing the at least one therapy electrode to deliver the therapy and after causing the indication that the therapy is about to be delivered to be provided, allow the patient to provide an input that causes the ambulatory medical device to refrain from delivering the therapy to the patient.

In some implementations, the cardiac condition is an arrhythmia condition.

In some implementations, selecting an operating mode includes selecting a motor vehicle operating mode.

In another aspect, an ambulatory medical device includes a monitoring component that includes at least one sensing electrode for detecting a cardiac condition of a patient. The ambulatory medical device also includes at least one processor configured for receiving an indication that the patient is in a wet environment. The at least one processor is also configured for selecting an operating mode of the ambulatory medical device based at least in part on the indication that the patient is in the wet environment.

Implementations can include one or more of the following features.

In some implementations, the operating mode is selected based on an input received by a user interface of the ambulatory medical device.

In some implementations, receiving an indication that the patient is in a wet environment includes detecting that a moisture level meets or exceeds a threshold.

In some implementations, the moisture level is detected by a moisture sensor of the ambulatory medical device.

Implementations can include one or more of the following advantages.

In some implementations, the patient can use the ambulatory medical device in multiple environments (e.g., while showering/bathing, while sleeping/sitting, while exercising, etc.) without compromising the efficacy of the ambulatory medical device's monitoring and/or treatment capabilities. Parameters for detecting a cardiac condition can be automatically adjusted to suit the environment such that the cardiac events are properly detected while reducing the likelihood of false alarms. For example, while in a water operating mode, the ambulatory medical device can reduce its sensitivity and/or wait for an extended amount of time before determining that a cardiac condition is occurring due to the heightened potential for false alarms in a wet environment.

In some implementations, sequences used by the ambulatory medical device for treating cardiac conditions can be based on the mode and/or environment that the ambulatory medical device is operating under. For example, when the ambulatory medical device is operating in the water operating mode (e.g., while the patient is taking a shower), the patient may be slow to respond to treatment warnings. The ambulatory medical device can afford the patient additional time to respond to a warning indicating that a treatment is about to be applied, thereby giving the patient an adequate chance to stop the treatment while in a potentially compromising environment.

In some implementations, the way by which the ambulatory medical device can provide alarms to and receive input from the patient is based on the current operating mode. For example, the ambulatory medical device may provide a relatively loud audible alarm when it is operating in the shower operating mode or the activity operating mode. The ambulatory medical device may provide a tactile alarm when it is operating in the sleep operating mode.

In some implementations, the ambulatory medical device can automatically enter an operating mode based on one or more environmental conditions identified based on input from one or more sensors. For example, the ambulatory medical device can automatically enter the water operating mode based on information received from a moisture sensor. The ambulatory medical device can automatically enter the activity operating mode or the sleep operating mode based on information received from a motion sensor and/or a pressure sensor.

Other features and advantages of the invention will be apparent from the drawings, detailed description, and claims.

DESCRIPTION OF DRAWINGS

The accompanying drawings are not intended to be drawn to scale. In the drawings, components that are identical or nearly identical may be represented by a like numeral. For purposes of clarity, not ever component is labeled in every drawing. In the drawings.

DETAILED DESCRIPTION

Figure 1:
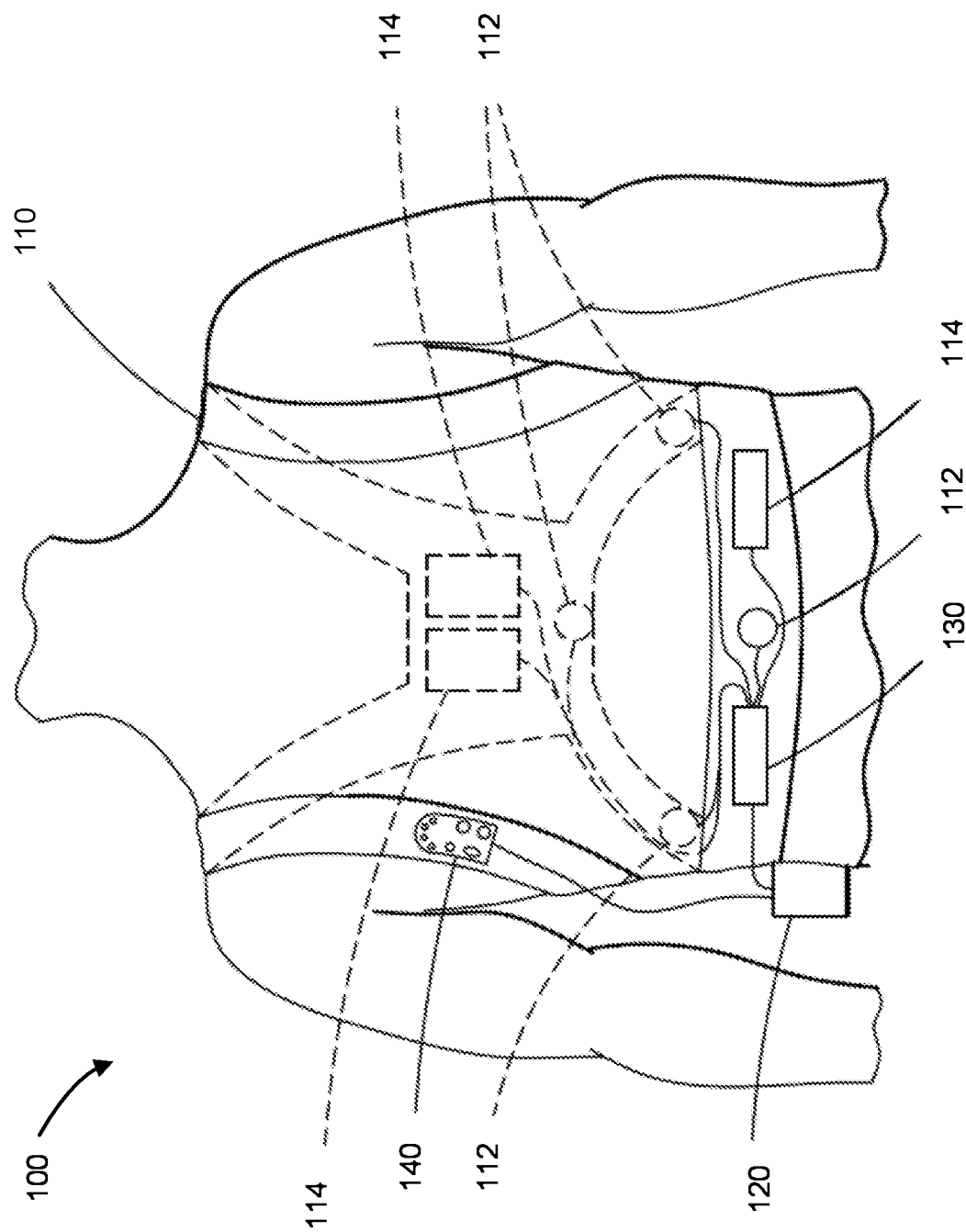
FIG. 1 is an example of a wearable medical device that includes a medical device controller.

A medical device for use with the systems and techniques as disclosed herein can be configured to monitor one or more cardiac signals of a patient and determine whether the patient may be experiencing a cardiac condition. For example, the medical device can include a plurality of sensing electrodes that are disposed at various locations of the patient's body and configured to sense or monitor the cardiac signals of the patient. In some implementations, the medical device can be configured to monitor, in addition to cardiac signals, other physiological parameters as described in further detail below. For example, the medical device can be used as a cardiac monitor in certain cardiac monitoring applications, such as mobile cardiac telemetry (MCT) and/or continuous event monitoring (CEM) applications.

In some implementations, the medical device can be configured to determine an appropriate treatment for the patient based on the sensed cardiac signals and cause one or more therapeutic shocks (e.g., defibrillating and/or pacing shocks) to be delivered to the body of the patient. The medical device can include a plurality of therapy electrodes that are disposed at various locations of the patient's body and configured to deliver the therapeutic shocks.

A medical device as described herein can be configured to monitor a patient for an arrhythmia condition such as bradycardia, ventricular tachycardia (VT) or ventricular fibrillation (VF). While the detection methods and systems described hereinafter are disclosed as detecting VT and VF, this is not to be construed as limiting the invention. Other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In some implementations (e.g., implementations in which the medical device is a treatment device, such as a pacing and/or a defibrillating device), if an arrhythmia condition is detected, the medical device can automatically provide a pacing or defibrillation pulse or shock to treat the condition.

In some implementations, a medical device can be configured to dynamically and/or adaptively adjust one or more operational parameters of the medical device in response to patient, environmental and/or contextual conditions. For example, dynamically adjusting operational parameters includes adjusting the operational parameters in substantially real-time as changes in the underlying patient, environmental and/or contextual conditions occur. For example, the operational parameters may be adjusted after a delay from when a change in an underlying patient, environmental and/or contextual condition occurs. In some implementations, the delay may be based on a predetermined value. In some implementations, the delay is user-configurable and provided through a user interface.

For example, a medical device can be configured to operate in a default operating mode and one or more of a plurality of special modes in response to the patient, environmental and/or contextual conditions. Changes to the one or more operational parameters and/or an operating mode in which the medical device operates can be based on the monitored patient signals (e.g., cardiac or other physiological signals of the patient), and/or a selection input provided by a user and received at the medical device.

For example, the one or more operational parameters may include sensing and/or monitoring parameters. Such sensing and/or monitoring parameters can include detection parameters, criteria and/or conditions (e.g., patient thresholds) that, if met, may indicate that the patient is experiencing a medical condition. For example, a cardiac monitoring and/or treatment device may detect one or more cardiac conditions based on such a set of operational parameters. Similarly, operational parameters can include treatment parameters that control a therapy delivered by the device. For example, such treatment parameters may control an intensity or a manner of therapy delivery. As described in detail below, medical devices described herein may be configured to adjust its operational parameters in response to changing patient, environmental, and/or contextual conditions. Other types of device operational parameters may be adjusted or modified in response to changing conditions based on the principles described herein. For example, such parameters can include, without limitation, communication parameters (e.g., for controlling the transmission of data to and from the medical device), alarm and notification parameters (e.g., for controlling the types, manner, and modes of alerting the patient, bystanders, and/or caregivers), and/or other device operating parameters (e.g., relating to battery circuit parameters, device self-monitoring and testing parameters, energy storage parameters, etc.).

For example, a medical device may be configured to adjust one or more operational parameters based on a predetermined relationship with one or more input signals from one or more sensors associated with the medical device. For example, such adjustments may be made dynamically and automatically in response to changing conditions. For example, the adjustments may occur within an open or closed loop system control scheme. Further, such adjustments may be made adaptively in response to learning patterns in the underlying changing conditions.

A predetermined relationship between the operational parameters and input sensed signals as described above may be based on any known or learned relationship between the underlying parameters, including single or multi-variable linear, non-linear (such as quadratic, logarithmic, exponential, etc.), and other kinds of relationships. In some cases, the predetermined relationship may be based on binary classifications, transformations of the underlying signals (e.g., discrete forms, frequency and/or other domains, etc.), and/or statistical analysis. In some examples, the relationship may be based on performing a multivariate regression analysis of the input sensed signals and deriving one or more equations to describe the relationship.

Additionally, one or more techniques may be employed to match, verify, and/or correlate information from one or more types of sensors against other types of sensors. For example, if a patient is performing a physical activity such as running or jogging, the heart rate sensor information may be correlated with accelerometer information to confirm the activity and the intensity of the activity.

The medical device may also be configured to analyze a plurality of input signals in order to adaptively effect changes to one or more underlying operational parameters. For example, the medical device may effect changes to the operational parameters based on a series of decision nodes. Each node may be based on logic implemented to test one or more input signals (individually or in a predetermined combined format) from one or more sensors of the medical device against a threshold. An output of such decision nodes may cause one or more operational parameters of the medical device to be increased, decreased, or otherwise adjusted.

In some implementations, machine learning classification or regression tools may be trained and validated on training/validation populations of sensed values corresponding to signals from the one or more sensors. Such machine learning based systems can be implemented in accordance with the principles described herein such that the medical device can adaptively adjust its operational parameters in accordance with changing patient, environmental, and/or contextual conditions.

For example, in some implementations, a machine learning based classifier model (e.g., a random forest classifier model) may be trained and validated on metrics relating to patient response button use (or other response mechanism) and corresponding ECG signals of the patient during periods when the patient response buttons are used. Such a model can assess times at which patients push the response buttons and the corresponding ECG signals to determine if the patient is conscious or undergoing a treatable condition. Once trained, the model can be adaptively validated and its corresponding thresholds can be adjusted over time for assessing new input response button uses and corresponding ECG signals. In this way, the device can use machine learning to adaptively learn whether a treatable condition is likely when the device detects that the patient has pushed the response buttons based on prior historical data about the individual patient or a population of patients.

Any of the above techniques can be used alone or in combination in order to establish a relationship between the operational parameters of the medical device and the sensed signals. In some situations, such techniques may be implemented within the one or more special operating modes as described herein.

Cardiac Devices

In one implementation, a cardiac monitoring and/or treatment device may adjust its operational sensing or monitoring parameters in response to changing conditions and/or patient input as described below. The cardiac device may be configured to monitor a patient's cardiac signals, including ECG signals, heart sounds, etc. For example, the cardiac device may include an axis analyzer to derive a signal representation of the electrical axis of the heart of a patient from whom ECG signals are received. Changes in the signal representation of the electrical axis of the heart can be evaluated to determine whether a treatable condition exists (e.g., the patient is experiencing a cardiac condition). For example, the signal representation can include a magnitude component and a phase component. In some examples, the phase component can indicate a zero-crossing indication. In some implementations, the analyzer can use a complex matched filter to analyze the ECG signals.

A treatable condition can be determined based on changes in the heart axis information from a patient normal condition (e.g. baseline values, such as a baseline ECG recording). In this regard, a patient monitored by the medical device may undergo an initial baselining process. During the baselining process, a baseline set of information relating to the patient is captured. For example, a baseline ECG recording may be obtained. The baseline ECG may have a length of approximately 30 seconds to one minute. The baseline ECG values are fed into the analyzer in the form of filter coefficient values corresponding to the filters used in the analyzer. In particular, one or more specific comparisons of an incidence of zero phase crossing with periods of peaks of the magnitude component of the heart axis representation can be used to indicate the treatable condition. When the analyzer determines that a treatable condition exists (e.g., the patient is experiencing a cardiac condition), the analyzer can set a flag to indicate the condition. Additional details concerning a method for determining treatable conditions are disclosed in U.S. Pat. No. 5,944,669 (the "'669 patent") entitled "Apparatus and method for sensing cardiac function," the contents of which are incorporated herein in its entirety.

In a default operating mode, once the baseline filter coefficients values are input to the analyzer, the analyzer continuously monitors the phase component for zero crossing conditions and when detected, the analyzer checks the magnitude component to determine whether the magnitude component is also above a magnitude threshold value. For example, the magnitude threshold value may be automatically calculated based on a prior history of the signal. Because amplitudes can vary according to a quality of the signal, the magnitude threshold value is allowed to vary within a preset of programmable range of values. In an example, the magnitude threshold value can be set to less than 90% of a previously detected peak level of the magnitude component.

In some examples, a sensitivity of the analyzer can be increased or decreased to reduce a number of false positives due to increased patient movement and/or activity. For example, changes to the sensitivity can be made by changing corresponding parameters of the analyzer dynamically in response to the patient movement and/or activity. Patient movement and/or activity can be detected through one or more sensors such as accelerometers, gyroscopes, tilt sensors, and the like. For example, a heart sounds sensor (e.g., which can be included in the wearable garment and/or associated components) may detect increased heart sounds activity indicating that the patient is performing an activity. The sensor data can be correlated with data from other sources to confirm that the patient is performing an activity and provide information related to the intensity of the activity. An intensity of the movement can be detected through one or more of such sensors. In some implementations, one or more parameters of the analyzer can be adjusted in a predetermined relationship with the input from the one or more sensors. As described above, a variety of other ways to control the operational parameters of the device may be employed including, for example, machine learning and statistical techniques, among others.

In order to increase or decrease the sensitivity of the analyzer, for example, phase detection and/or magnitude threshold parameters can be changed using any of the above techniques.

In some examples, to achieve decreased sensitivity (e.g., where an intensity of signal noise or patient movement increases), it may be desirable to relax the requirements for declaring a match with baseline values. For example, the device may allow for more matching with one or more baseline values (e.g., to increase matching the received ECG signal with the baseline ECG recording, obtained as described above). To allow for more frequent matching with baseline values, one or more phase detection parameters can be changed. For example, a zero crossing range can be increased from a default range such that the zero crossing condition detection rate is generally higher than the zero crossing condition detection rate in the default operating mode. In some examples, the magnitude threshold parameters can be changed. For example, the magnitude threshold value can be allowed to vary within a greater programmable range of values. For example, the magnitude threshold value can be set to 70-80% of a previously detected peak level of the magnitude component. In some examples, the detection parameters may be changed when the device is in one or more special operating modes, such as a water or activity mode. When the device is operating in a special operating mode, a sensitivity of the analyzer can be decreased in a manner similar to that described above (e.g., to reduce a number of false positives due to increased patient movement and/or activity). For example, phase detection and/or magnitude threshold parameters can be changed. In some examples, to allow for more frequent matching with baseline values, one or more phase detection parameters can be changed. For example, a zero crossing range can be increased from a default range such that the zero crossing condition detection rate is generally higher than the zero crossing condition detection rate in the default operating mode. In some examples, the magnitude threshold parameters can be changed. For example, the magnitude threshold value can be allowed to vary within a greater programmable range of values. For example, the magnitude threshold value can be set to 70-80% of a previously detected peak level of the magnitude component.

In some examples, it may be desirable to increase a sensitivity of the analyzer (e.g., by decreasing a zero crossing range from a default range such that the zero crossing condition detection rate is generally lower than the zero crossing condition detection rate in the default operating mode. For example, the magnitude threshold value can be configured to vary within a lesser range of values (e.g., 95% of the previously detected peak level of magnitude component).

Depending on patient, environmental, and/or contextual conditions, the device can be configured to automatically change a method of calculating one or more patient metrics. As such, there may be additional operational differences in one or more operating modes of the device. For example, as described in the '669 patent, in a default operating mode, a heart rate detector may be employed to determine whether the patient's heart rate is elevated. For example, a QRS detector can analyze signals from front-to-back (FB) electrodes and side-to-side (SS) electrodes and calculate FB and SS rates. These rates can be combined with an axis rate as determined by the axis analyzer and fed into a rate analyzer to provide final heart rate information. In some implementations, the heart rate can be calculated by averaging a rate obtained over a certain number of beats (e.g., five beats). For example, the averaging technique may be used in a default operating mode. When the patient is physically active, however, the heart rate can be based on a median value calculated from the multiple (e.g., five) beats. As such, when the device detects that the patient activity level has increased (e.g., beyond a predetermined threshold), the method of calculating the patient's heart rate information may automatically change. Similarly, in an activity operating mode, the method of calculating the heart rate may change.

In some implementations, when operating conditions change, a number of beats used for calculating the heart rate as described above can be increased relative to the number of beats used by default. For example, the device may use eight, ten, or more beats to calculate the heart rate and thus be able to ride through noisy signals and/or events that may be encountered during certain operating conditions. In some implementations, such as instances involving certain other special operating conditions, it may be desirable to reduce a number of beats used to less than what is used in the default operating mode.

The device may be automatically or manual put in a special operating mode (e.g., a water, activity, or other mode), depending on operating conditions. While operating in a special operating mode, for example, a number of beats used for calculating the heart rate as described above can be increased from what is used in a default operating mode. For example, the device may use eight, ten, or more beats to calculate the heart rate and thus be able to ride through noisy signals and/or events that may be encountered during operation in the special mode. In some implementations, such as instances involving certain other special operating modes, it may be desirable to reduce a number of beats used to less than what is used in the default operating mode.

The operational sensing, monitoring, and/or detection parameters can include heart rate parameters. For example, while operating under certain operating conditions, heart rate thresholds may be changed in accordance with one or more principles as described herein. As background, if the patient's heart rate is sustained in an elevated zone as determined based on predetermined rate thresholds, then the patient may be experiencing a VT or VF event (e.g., assuming other detection parameters are also met as described above). For example, the predetermined rate thresholds can be input to the device via a user interface module during initial setup for the device. For instance, the predetermined rate thresholds may be set to a default value (e.g., 150 beats per minute for a VT type event, and 200 beats per minute for a VF type event). The default value may be adjusted to a new value (e.g., 160 beats per minute for a VT type event, and 210 beats per minute for a VF type event) via a user interface module.

In some implementations, while operating under certain operating conditions, the predetermined rate thresholds may be increased or decreased as appropriate depending on changes in the underlying operating conditions. For instance, if the patient is jogging or otherwise exercising, then the predetermined rate threshold may be configured to increase by a predetermined amount (e.g., five or ten beats per minute over the rate thresholds set for the default operating mode). As the patient's exercise intensity increases or decreases, the number of beats used in the calculation may be increased or decreased.

In some implementations, while operating under a special operating mode, the predetermined rate thresholds may be increased or decreased as appropriate. For example, if the special operating mode is an activity mode (such as when the patient is jogging or otherwise exercising), then the predetermined rate threshold may be configured to increase by a set amount (e.g., five or ten beats per minute over the rate thresholds set for the default operating mode).

In some implementations, the device can employ a spectral analyzer that uses fast Fourier transform (FFT), or other techniques, to measure and evaluate the respective SS and FB ECG input signal frequency components. For example, the presence of certain spectral components can be indicative of certain cardiac conditions as noted in detail below. While operating in a default operating mode, the device may use a single FFT analysis to provide an indication of a cardiac condition. Under some operating conditions, the device may use a plurality (e.g., several) FFT analyses to declare the condition. For example, the number of FFT analyses may increase or decrease depending on the underlying changes in the operating conditions. Similarly, while operating under some special operating modes, the device may use a plurality (e.g., several) FFT analyses to declare the condition.

Changes in Cardiac Signal Noise Analysis

As noted above, the detection parameters for determining whether the patient may be experiencing a cardiac condition may vary depending on the operating conditions. For example, while operating in a shower or water operating mode, the medical device may reduce its sensitivity by changing one or more health metric thresholds (e.g., an ECG score as described in further detail below). In some examples, the medical device may reduce its sensitivity by increasing an amount of detection time the device gives its noise algorithm (e.g., as explained in further detail below) to determine whether an identified event is a treatable VT/VF event. While operating in the shower or water operating mode, the cardiac signals received by the medical device may not be completely authentic. For example, the cardiac signals may be affected by the wet environment or excessive patient movements in the shower and take on an appearance that is different than what it would be under more typical conditions. The reduced sensitivity can account for potentially inaccurate ECG signals. For example, if the value meets or transgresses the modified thresholds or if the device persists in declaring a treatable VT/VF event after an extended detection time, the medical device may determine that the patient may be experiencing a cardiac condition.

In some implementations, after the analyzer has detected a cardiac condition, a noise detector can be executed to confirm the condition. For example, the noise detector can verify the detected condition to distinguish a treatable cardiac condition from inappropriate sensing of, for example, a VT/VF condition due to noise caused by lead malfunction, electromagnetic interference, patient movement, etc. For example, a transformed version of the patient's ECG signal, such as a frequency domain representation of the signal, can be analyzed, a value representing at least one feature of the transformed ECG signal can be extracted, and an ECG score can be determined based on the at least one feature of the transformed ECG signal. The transformed ECG signal can then be compared to a threshold. For example, the transformed ECG signal may be a presentation of a power distribution of the signal over a range of frequencies, which can be calculated from, for example, a frequency domain representation of the ECG signal. For example, the transformed ECG signal can be a power spectral density (PSD) signal, which describes how the power of the ECG signal is distributed over different frequencies. For example, the noise detector may generate the PSD by performing fast Fourier transform (FFT) operations on the time domain ECG signal, or the noise detector may employ other discrete Fourier transform (DFT) techniques to generate the PSD.

For example, a PSD of an ECG signal demonstrating VT/VF typically has distinct features. For example, the PSD of an ECG signal demonstrating VT/VF may have several distinct dominant spectral bands, while a normal sinus rhythm may have a dominant spectral band at less than 2.5 Hz. The dominant spectral band is the band of frequencies that correspond to a maximum value of the PSD. A PSD with multiple dominant spectral bands has more than one band of frequencies in which the power of the ECG signal is significant. The information content in the PSD of the ECG signal that is in VT/VF is spread over more frequencies, and the frequency content is most dense around the frequency of the VT, which is typically greater than 2.5 Hz.

In addition, even in the presence of a substantial amount of noise, a PSD of normal sinus rhythm differs from a PSD of VT/VF arrhythmia. Noise within the ECG signal may be characterized as entropy (i.e., randomness). Accordingly, various entropy calculations may be performed on a PSD to differentiate between a normal sinus rhythm signal with noise and a VT/VF signal. For example, an in-band entropy may be calculated for a PSD of an ECG signal as described in co-pending U.S. application Ser. No. 14/791,836 (the "'836 application"), published as U.S. Patent Publication No. 2016/0000349, filed Jul. 6, 2015, entitled "SYSTEM AND METHOD FOR DISTINGUISHING A CARDIAC EVENT FROM NOISE IN AN ELECTROCARDIOGRAM (ECG) SIGNAL," the entire contents of which are hereby incorporated by reference. The first-band entropy may be calculated by converting the PSD to a probability distribution function (PDF) and calculating the entropy of the signal between 0 Hz and 2 Hz. The four features of the PSD (a dominant frequency of the PSD; in-band entropy of the PSD between frequencies of 2 Hz and 6 Hz; first-band entropy of the PSD between frequencies of 0 Hz and 2 Hz; and a variance of the PSD, which is extracted as described below) were selected as the features that would be extracted from the PSD and submitted to a machine learning classifier based on a combination of feature selection experimentation and physiological reasoning.

When a normal sinus rhythm (NSR) in the absence of noise is compared to an NSR contaminated with motion artifact or machine noise, some characteristics of the PSD remain the same. For example, because entropy is a measure of randomness, the entropy in the 0-2 Hz range of the PSD is similar for an NSR with and without noise. However, the PSD for an NSR without the presence of noise typically has much less information content in the 2-6 Hz range than a PSD for an NSR with a noisy signal. Variance can be selected as a feature that would be extracted from the PSD and submitted to the machine learning classifier because the variance of a distribution provides a "feel" for the relative spread of the distribution. If a PSD has most of the energy in the 0-2 Hz band and very little energy in the 2-6 Hz band, the variance is relatively small. However, a PSD with much energy in the 2-6 Hz band would provide a much wider variance of the PSD. A PSD for an NSR has most of the energy in the 0-2 Hz band, and a PSD for a VT/VF arrhythmia has more energy in the 2-6 Hz band. In order to calculate variance, it can be assumed that the PSD is a normal distribution, and the variance of the PSD is calculated by treating the PSD as a PDF and calculating the second moment.

After the features are extracted from the PSD, the features can be fed into the machine learning classifier. For example, as described in the '836 application, the classifier may be trained on data sets including noisy normal sinus rhythm signals (e.g., false positive detections) and tachyarrhythmia signals. For example, two classifiers for each detection channel (e.g., side-to-side channel and front-to-back channel) can be used, where each classifier produces a numerical value in a range from 0 to 1. For example, a 20-second buffer of an ECG signal is passed from a shared memory to be analyzed. An ECG score is compiled based on the outputs from the evaluation of each second of analysis as a master score covering the 20 seconds of ECG signal. Fewer or additional ECG signal can be used in evaluating the ECG score (e.g., the analysis can span a few seconds to multiple minutes, hours, or even days).

While operating in a default operating mode, for example, a threshold score for the noise classification can be selected to have a value of 10. That is, if the score is above 10, then the noise detection confirms the cardiac condition. Control then passes to the treatment sequence. However, if the score is less than 10, then the event can be classified as noise and the treatment sequence can be held off while a new score is created based on continued monitoring. If the score goes above 10, then the treatment sequence is initiated.

Under certain operating conditions, such as when the patient is in the shower or performing an activity, a sensitivity of the noise detector can be decreased (e.g., and a specificity can be increased) to reduce a number of false positives due to increased patient movement and/or activity. For example, adjustments may be made dynamically or automatically in relation to the level or intensity of the humidity exposure and/or the activity. In some examples, the threshold ECG score can be raised (e.g., to 12, 15 or more) depending on the input signals from the sensors. For example, as a humidity sensor senses high humidity and/or water levels, the threshold ECG score may be automatically raised according to a predetermined relationship with the level of detected humidity. Similarly, as a motion sensor senses increased or decreased patient physical activity and/or movement, the threshold ECG score may be automatically raised or decreased according to a predetermined relationship with the level of detected activity or movement.

In some examples, the device may be put in a special operating mode under certain operating conditions. As such, in one of the special operating modes, (e.g., a water or activity mode as described herein), a sensitivity of the noise detector can be decreased (e.g., and a specificity can be increased) to reduce a number of false positives due to increased patient movement and/or activity. In one example, the threshold ECG score can be raised (e.g., to 12, 15 or more). For example, the threshold ECG score for the special operating mode can be preset by a user through a user configuration screen (e.g., during an initial fitting and/or baselining process). In some implementations, such as instances involving certain special operating modes, a sensitivity of the noise detector can be increased (e.g., by decreasing the threshold ECG score to be less than the threshold ECG score in the default operating mode. In some implementations, the threshold ECG score can be decreased to 8, 7, or less.

In some implementations, the cardiac signal can undergo one or more preprocessing and/or noise detection steps (e.g., based on a machine learning classifier algorithm), and in some implementations, the ECG score may be processed or converted into a different form before it is compared to the threshold. If the ECG score meets or exceeds the threshold, the medical device may determine that the patient may be experiencing a cardiac condition.

Changes in Device Treatment Parameters

After it is determined that the patient may be experiencing a cardiac condition, the medical device can be configured to select a treatment sequence for treating the particular condition. Depending on the operating mode, for example, the medical device may be configured to determine that a series of defibrillation shocks at particular intensities is appropriate for treating the cardiac condition. In some implementations, the device can issue up to five bi-phasic shocks if the device determines that the cardiac condition is present after each preceding shock.

For each of the special operating modes, a caregiver or other designee can change, via a user interface module, a number of pulses, or shock treatment parameters for each of the five pulses. For example, the user may set a water mode treatment sequence to include all five bi-phasic pulses, and may set each of the pulses to be delivered with escalating energy levels.

In certain operating conditions, the treatment parameters may have a predetermined relationship with the signals from the environmental, contextual, and/or patient sensors. As the sensed signals from the sensors change over time, the treatment parameters may be dynamically adjusted to conform to the current operating condition. In some examples, depending on the sensed signals, the treatment parameters may be adjusted to deliver more or less energy per pulse to the patient as the patient and/or the environment in which the device operates changes. Similarly, one or more profiles and/or shapes of the pulse may be dynamically shaped or adjusted in response to the operating conditions.

Changes in Alarms and/or Notifications

The medical device may provide one or more indications (e.g., warnings or alerts) to the patient that a treatment shock is about to be delivered before it is actually delivered to the patient. The one or more indications may be in various forms. For example, one or more indications may be haptic, and one or more indications may be audible. In some implementations, a first indication is a haptic indication that is intended to attract the patient's attention without disturbing others, a second indication is a low volume audible alert, and a third indication is a high volume audible alert.

In some implementations, as the operating conditions change over time, any or all of the duration and/or number, and/or types of indications, and/or sequence of indications may be dynamically changed or adjusted in accordance with a predetermined relationship with one or more sensed signals. For example, as the patient's activity increases, it is less likely that the patient will be able to respond quickly to certain alarms. As such, an amount of time provided to respond to an alarm may be increased in proportion to the amount of detected activity. Similarly, an intensity of an audible alarm may automatically increase in proportion to an amount of detected ambient noise.

In some implementations, for each of the default and/or special operating modes, all of the duration and/or number, and/or types of indications, and/or sequence of indications can be user configurable via a user interface. For example, a caregiver may determine that for a particular patient it is desirable to, in a patient sleep mode, skip the haptic alarm and proceed directly to the low-volume audible alarm. In addition, the caregiver may lengthen the duration of the low-volume audible alarm in the patient sleep mode relative to the duration of the low-volume audible alarm in the default mode for the patient. Additional techniques for adapting alarms according to one or more detected conditions are disclosed in U.S. Patent Publication No. 2012/0293323 (the "'323 publication"), entitled "System and method for adapting alarms in a wearable medical device," the contents of which are incorporated herein in their entirety.

On perceiving the alarm, the patient may be able to instruct the medical device to refrain from delivering the treatment shock. For example, the patient may instruct the medical device to refrain from applying a treatment shock if the patient is well and the medical device falsely identified a cardiac event. Information related to the initial treatment determination, the indication that the treatment is about to be delivered, and the way by which the patient can stop the treatment from occurring is generally referred to as the treatment sequence.

The treatment sequence may be selected based at least in part on the particular mode that the medical device is operating under at the time. For example, while operating under a default operating mode, the medical device may give the patient 30 seconds to stop a selected treatment from being applied. In contrast, while operating under a special (e.g., non-default) operating mode (e.g., a water or activity mode), the medical device may give the patient an extended amount of time (e.g., 45 seconds) to stop a selected treatment from being applied.

Example Medical Devices

In some implementations, the medical device as described herein is an external or non-invasive medical device (e.g., in contrast to internal or invasive devices, such as implantable medical devices). For example, the external medical device can be a cardiac monitoring and/or automated pacing device or defibrillator, such as an in-facility continuous monitoring defibrillator (e.g., for patients that are confined to a limited space within a facility, such as, within a hospital environment, to a patient's room) or an outpatient wearable defibrillator.

In some implementations, an external medical device can be an automated cardiac monitor or defibrillator that can be used in certain specialized conditions and/or environments such as in combat zones or within emergency vehicles. The medical device can be configured so that it can be used immediately (or substantially immediately) in a life-saving emergency. For example, the external medical device can be an automated external defibrillator (AED). Such AEDs are available from ZOLL® Medical Corporation of Chelmsford, MA.

In some implementations, the external medical device is an ambulatory device (e.g., a device that is capable of and designed for moving with the patient as the patient goes about his or her daily routine). In some examples, the external medical device can be configured as a wearable defibrillator, such as the LifeVest® wearable defibrillator available from ZOLL® Medical Corporation of Chelmsford, MA.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, the devices described herein may be capable of being used or worn by, or attached or connected to a patient for example, up to hours or beyond (e.g., weeks, months, or even years).

In some implementations, the devices described herein may be removed for a period of time before use, wear, attachment, and/or connection to the patient is resumed (e.g., to change batteries, to change the garment, and/or to take a shower), without departing from the scope of the examples described herein.

The devices as described herein may be capable of continuously, substantially continuously, long-term and/or extended monitoring of a patient. For example, devices as described herein may be capable of providing cardiac monitoring without substantial interruption for a predetermined period of time. In some examples, the devices described herein may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, the devices described herein may be powered down for a period of time before monitoring is resumed (e.g., to change batteries, to change the garment, and/or to take a shower), without departing from the scope of the examples described herein.

In some instances, the device may carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

In some implementations, the medical device as described herein can be a hospital based medical device including, for example, a cardiac monitoring device, a defibrillator and/or pacing device. For example, the hospital based device can include a defibrillator and/or pacing device configured for continuous or substantially continuous use, wear, connection, attachment, or monitoring by/to/of a patient in a hospital environment. The hospital based device can include a plurality of therapy and sensing electrodes that are attached to the patient's skin. In some examples, the sensing and/or therapy electrodes are disposable adhesive electrodes. In some implementations, the electrodes are affixed to an electrode assembly (e.g., a patch), which can then be adhesively attached to the patient's skin. The sensing and/or therapy electrodes, and/or integrated electrodes can be attached to the patient's skin at particular locations as prescribed by a trained professional.

In some implementations, the medical device as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (e.g., a patch) that can be adhesively attached to the patient's skin. The patient may replace the electrodes and/or patches as prescribed by a trained professional.

For example, the medical device can include a user interface for interacting with the medical device. The device can include one or more input mechanisms (e.g., buttons) that the patient can interact with in order to respond to a treatment alert. In some examples, the medical device issues a treatment alert before providing a treatment shock, and if the patient does not respond to the treatment alert (e.g., by holding down one or more response buttons), the device can deliver the treatment shock to restore normal heart rhythm.

Example Wearable Medical Device

FIG. 1 illustrates an example wearable medical device 100. The wearable medical device 100 includes a plurality of sensing electrodes 112 that can be disposed at various positions about the patient's body. The sensing electrodes 112 are electrically coupled to a medical device controller 120 through a connection pod 130. In some implementations, some of the components of the wearable medical device 100 are affixed to a garment 110 that can be worn on the patient's torso. For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows three sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled to the medical device controller 120 through the connection pod 130. The therapy electrodes 114 are configured to deliver one or more therapeutic defibrillating shocks to the body of the patient if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached to or removed from the wearable medical device 100 as needed.

The controller 120 includes response buttons (210 of FIGS. 2A-2B) and a touch screen (220 of FIGS. 2A-2B) that the patient can interact with in order to communicate with the medical device 100. The controller 120 also includes a speaker (230 of FIGS. 2A-2B) for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient.

Figure 2A:
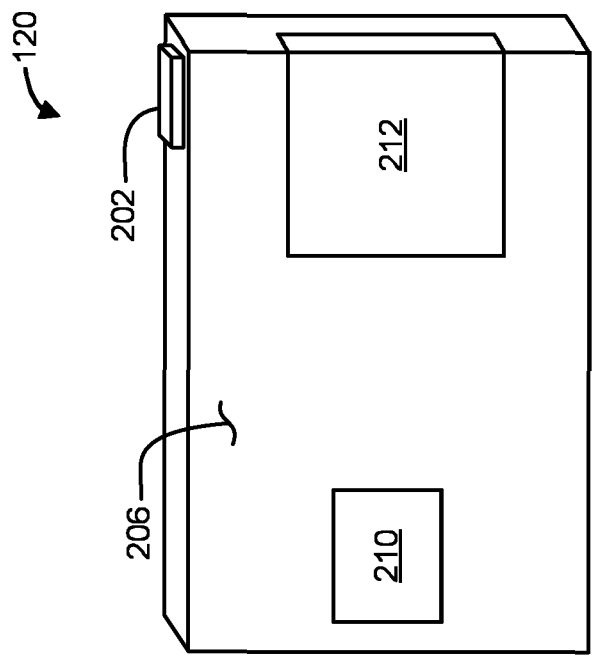
FIGS. 2A-2B show an example of the medical device controller of FIG. 1.

FIGS. 2A (front view) and 2B (rear view) show an example of the medical device controller 120 of FIG. 1. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 204 for communicating information to the patient, caregiver, and/or the bystander. The controller 120 includes one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. The medical device controller 120 may further include a port 202 to removably connect sensing electrodes (e.g., sensing electrodes 112) and/or therapeutic electrodes (e.g., therapy electrodes 114), and/or electrode patches, to the medical device controller 120.

Figure 2B:
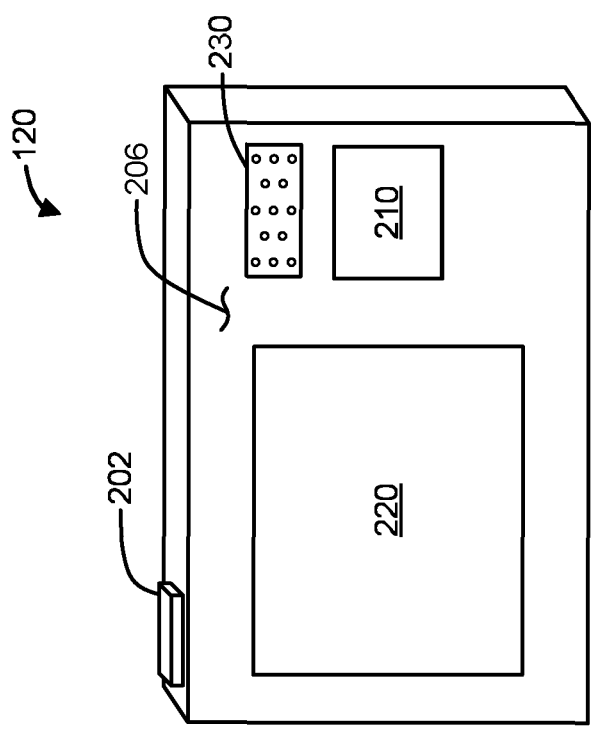
Figure 3A:
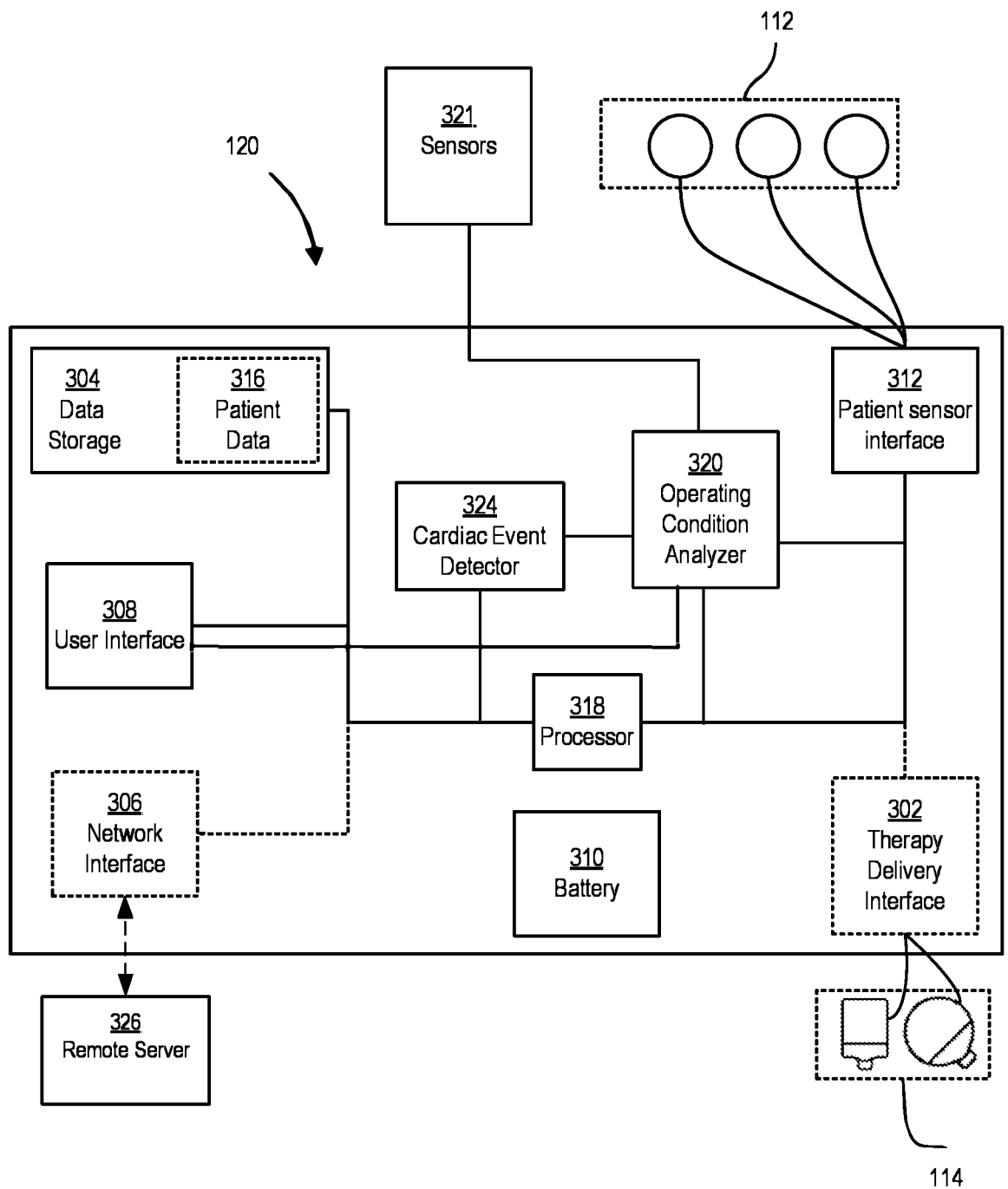
FIG. 3A is a functional schematic of the medical device controller of FIGS. 1 and 2A-2B.

FIG. 3A shows a schematic of an example of the medical device controller 120 of FIGS. 1 and 2A-2B. The controller 120 includes a processor 318, an operating condition analyzer 320, one or more sensors 321, a cardiac event detector 324, a patient sensor interface 312, an optional therapy delivery interface 302, data storage 304 (which may include patient data storage 316), an optional network interface 306, a user interface 308 (e.g., including the touch screen 220 shown in FIG. 2), and a battery 310. The patient sensor interface 312 is coupled to the patient sensing electrodes 112, and the therapy delivery interface 302 (if included) is coupled to the patient therapy or treatment electrodes 114. The patient sensor interface 312 and the therapy delivery interface 302 implement a variety of coupling and communication techniques for facilitating the exchange of data between the patient electrodes 112, 114 and the controller 120.

In some implementations, the processor 318 can perform a series of instructions that control the operation of the other components of the controller 120. The cardiac event detector 324 is configured to monitor the cardiac activity of the patient and identify cardiac events experienced by the patient based on received cardiac signals. In some examples, the cardiac event detector 324 can access patient baseline information in the form of templates (e.g., which may be stored in the data storage 304 as patient data 316) that can assist the cardiac event detector 324 in identifying cardiac events experienced by the particular patient, as described above. In some examples, the network interface 306 can facilitate the communication of information between the controller 120 and one or more other devices or entities over a communications network. In some examples, the network interface 306 is configured to communicate with a server (e.g., a remote server 326). A caregiver can access the data from the remote server 326 to access information related to the patient.

The operating condition analyzer 320 can be configured to, responsive to on one or more environmental and/or contextual conditions (e.g., as sensed by sensors 321) and/or the monitored cardiac signals of the patient (e.g., as sensed by electrodes 112) and/or a selection input provided by a user (e.g., through user interface 308), cause the controller 120 to change one or more operational parameters and/or an operation mode of the device 100.

For example, sensors 321 can include one or more sensors to detect operating conditions of the medical device including environmental and/or contextual conditions. The sensors 321 can include one or more of motion sensors, resistive potentiometers, capacitive sensors, differential transformers, accelerometers, humidity sensors, pressure sensors, position sensors, force sensors, shock sensors, piezo sensors, strain gauges, optical sensors, moving-coil sensors, temperature sensors, imaging sensors, electro-optical sensors, sound sensors, microphones, ultrasonic sensors, radiation sensors, and flow sensors, among others.

Example Monitoring Medical Device

In some examples, the medical device may be a patient monitoring device. For example, the patient monitoring device may be configured to monitor one or more of a patient's physiological parameters without an accompanying treatment component. For example, a patient monitor may include a cardiac monitor for monitoring a patient's cardiac information. The cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

Figure 3B:
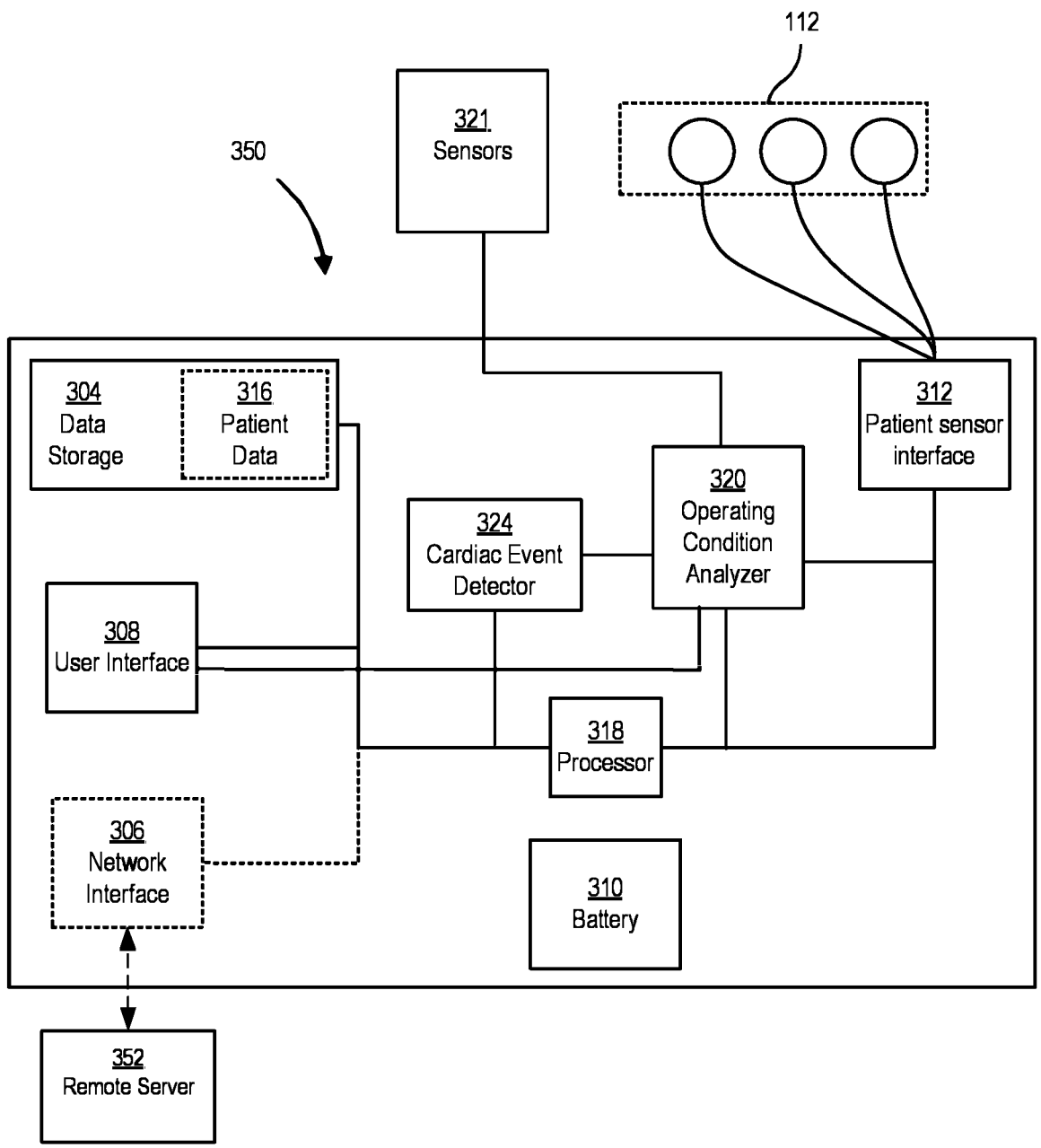
FIG. 3B is a functional schematic of an example of a cardiac monitor.

FIG. 3B illustrates an example cardiac monitoring medical device, for example, a cardiac monitor 350. In some implementations, the cardiac monitor 350 is capable of and designed for being worn by a patient who is at risk of developing cardiac problems, but who does not yet meet criteria to be outfitted with a medical device that includes a treatment component (e.g., a defibrillator). Thus, the cardiac monitor 350 may be prescribed so that continuous and/or event-based data can be sent from the cardiac monitor 350 to a server (e.g., the remote server 352). In some implementations, the remote server 352 is the same as the server (326 of FIG. 3A) described above. A caregiver can access the data from the remote server 352 and determine whether the patient is experiencing or has experienced a cardiac problem. In some implementations, after determining that the patient is experiencing a cardiac problem, the caregiver may instruct the patient to begin wearing a medical device with treatment capabilities.

The cardiac monitor 350 includes a medical device controller (e.g., a medical device controller similar to the controller 120 described above with reference to FIGS. 1 and 2A-2B) along with associated components. In an implementation, the medical device controller 120 operates in a similar fashion as described above. The cardiac monitor includes the plurality of sensing electrodes 112. In some examples, the sensing electrodes 112 can be an integral part of a housing structure of the cardiac monitor 350.

In some implementations, the patient can interact with the user interface 308 to identify a patient symptom. The user interface 308 may include a drop down menu or check list that allows the patient to select a particular symptom from a list. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac event detector 324 can cause a portion of patient physiological information (e.g., in the form of a cardiac signal) to be captured for a length of time that is based on a time at which the symptom was experienced. For example, the cardiac event detector 324 can cause a portion of an ECG signal of the patient to be captured. The portion of the ECG signal is sometimes referred to herein as an ECG strip. In some implementations, the cardiac monitor 350 can continuously record ECG data while simultaneously identifying and recording one or more ECG strips relating to one or more events of interest (e.g., patient-reported symptoms, events detected by the cardiac event detector 324, etc.). As such, if a caregiver wishes to view ECG data for a period of time prior to or after the recorded ECG strip relating to an event of interest, such data is available for review from the continuously-recorded ECG data.

The operating condition analyzer 320 can be configured to operate in a manner similar to that previously described in connection with FIG. 3A. Accordingly, the operating condition analyzer 320 can be configured to, responsive to on one or more environmental and/or contextual conditions (e.g., as sensed by sensors 321) and/or the monitored cardiac signals of the patient (e.g., as sensed by electrodes 112) and/or a selection input provided by a user (e.g., through user interface 308), cause the controller 120 to change one or more operational parameters and/or an operation mode of the device 100.

Dynamically Adjusting Operational Parameters

Figure 4A:
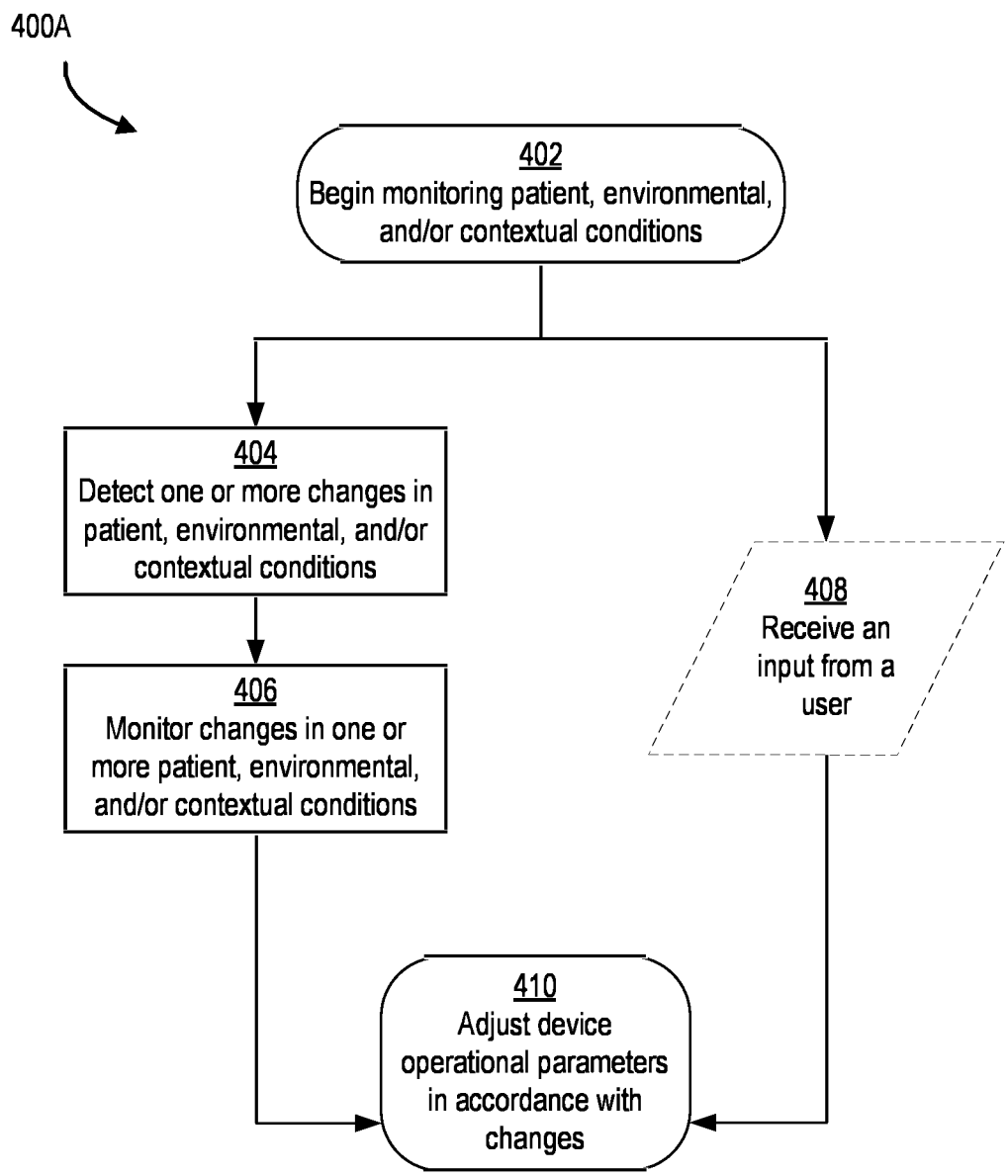
FIG. 4A is an example flow diagram illustrating a methodology for adjusting operational parameters of the wearable medical device.

FIG. 4A is an example flow diagram 400A illustrating a methodology performed to monitor one or more external sensors (e.g., the sensors 321 and/or the sensing electrodes 112 of FIGS. 3A-3B) and dynamically adjust device operational parameters in accordance with input from the external sensors. In this way, device operational parameters are adjusted in accordance with changes to patient, environmental, and/or contextual conditions. In some implementations, the methodology for adjusting one or more operational parameters can be initiated (block 402) by a triggering event, such as upon receiving an input from the user (block 408), or some other external event based on an input sensed signal received from one or more sensors or patient electrodes. In some implementations, one or more changes in patient, environmental, and/or contextual conditions are detected (block 404). For example, the input sensed signal may be a change in humidity or water sensed by a humidity and/or fluid sensor. Changes in one or more patient, environmental, and/or contextual conditions are monitored (block 406). A change in the humidity that meets or exceeds a predetermined threshold can initiate the process to adjust one or more device operational parameters in accordance with the changes (block 410). For example, the one or more operational parameters may be sensing and/or detection criteria as described in detail above. When an underlying predetermined change in one or more sensed signals is detected, the operational parameters may be adjusted according to a predetermined relationship with the one or more sensed signals.

In some implementations, the methodology for adjusting the operating parameters may be continuously running (e.g., the wearable medical device 100 is continuously in a state in which the operating parameters are adjusted in response to changing operating conditions). For example, the wearable medical device 100 can include one or more sensors such as a moisture sensor, a motion sensor (e.g., an accelerometer, a gyroscope, etc.), a pressure sensor (e.g., a strain gauge), and/or a location sensor (e.g., a GPS receiver). The wearable medical device 100 can receives signals from the one or more sensors, and the processor 318 can process the signals to ascertain environmental data (e.g., information related to environmental conditions.) The wearable medical device 100 can also monitor input (e.g., cardiac and/or other patient physiological signals) received from the patient sensors.

Over a period of time, the device 100 can monitor changes in the patient, environmental, and/or contextual conditions, and increases or decreases values corresponding to the one or more operating parameters in accordance with a predetermined relationship.

Figure 7A:
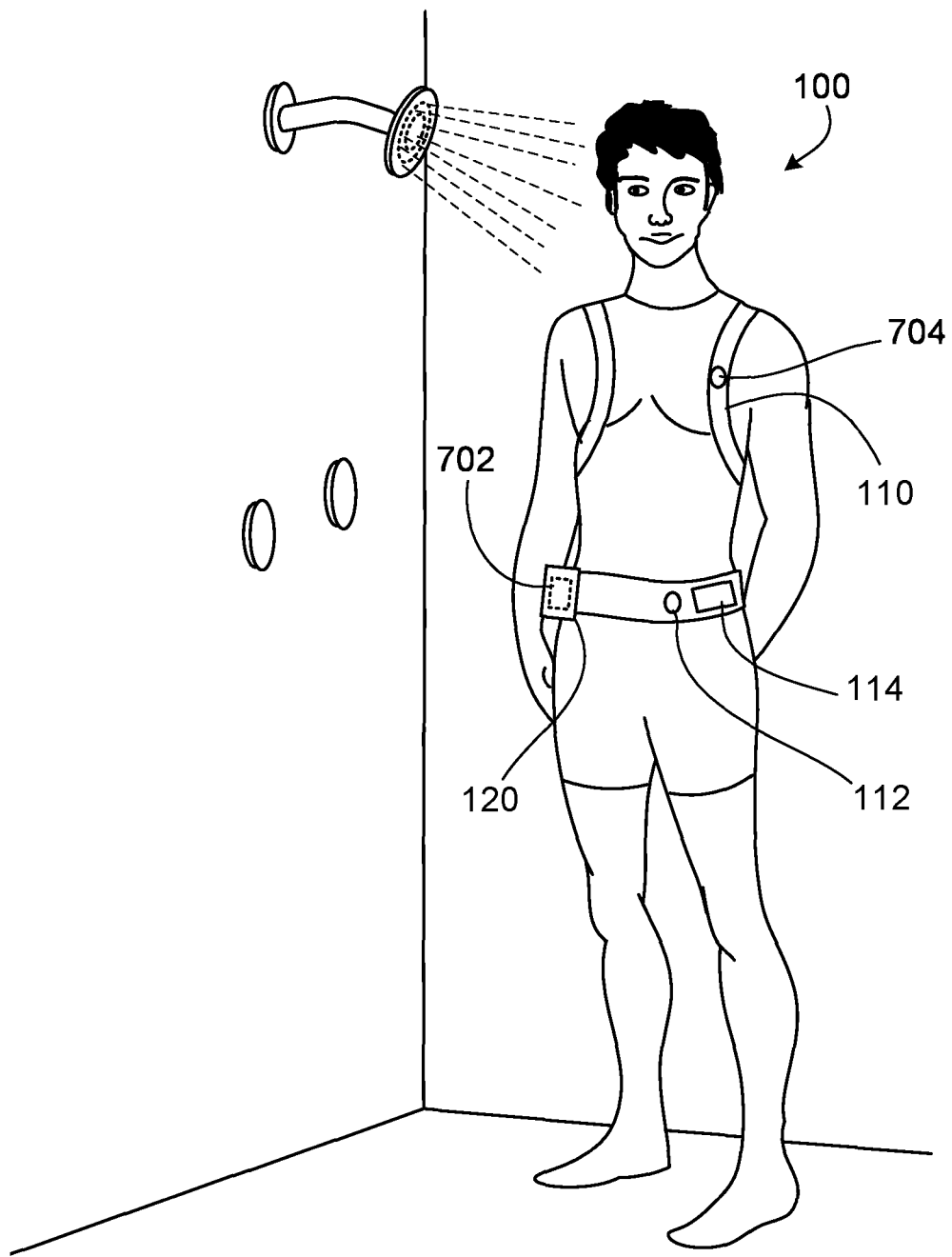
FIG. 7A shows an example of the wearable medical device being used in the shower.

For example, briefly referring to FIG. 7A, a moisture sensor 702 of the wearable medical device 100 may provide a signal to the processor 318 that indicates that the patient is in a humid environment (e.g., in the shower). As the signals received from the moisture sensor 702 indicate changing moisture content over a period of time, the wearable medical device 100 may automatically adjust (e.g., increase or decrease) a sensitivity of the cardiac detection algorithm in the manner described above.

In some implementations, the wearable medical device 100 also monitors cardiac signals received by the sensing electrodes 112 and considers these signals instead of or in addition to the environmental condition data in adjusting the operational parameters. For example, if the cardiac data indicates that the patient's heart rate is in an elevated state, then the device may cause the sensitivity of the cardiac detection algorithm to decrease according to a predetermined relationship with the amount of heart rate elevation. For example, if motion sensors detect that the patient is performing a vigorous activity, the cardiac detection parameters may be dynamically changed to decrease the sensitivity of the cardiac detection algorithm. For example, if the patient's heart rate is at or around 20% over the patient's regular average heart rate, the arrhythmia heart rate threshold may be correspondingly raised by 5% of the previous threshold. Similarly, if the patient's heart rate is at or around 20% over the patient's regular average heart rate, the amount of time to declare an arrhythmia event may be correspondingly increased by 10% of the previous threshold to give the device more time to analyze the ECG signal. Various other configurations may be employed where the level of activity (e.g., as detected by motion sensors) and/or the patient's current heart rate may have a predetermined relationship with the sensing and/or detection criteria. Thus, the timing threshold may be dynamically increased or decreased depending on the patient's activity. In this manner, changes in the output signals from the activity sensors and/or the heart rate sensors can act as a surrogate for the level of noisy artifacts in the ECG signal.

In some implementations, a user may be able to manually adjust one of more of the device operational parameters (block 408). For example, a user can manually cause the wearable medical device 100 to adjust the detection and/or treatment criteria using one or more input mechanisms, such as the touch screen 220 and/or a button on the medical device controller 120 and/or input mechanisms on other components of the wearable medical device (e.g., on the user interface pod 140).

Before, during, and/or after operating parameters are adjusted, the wearable medical device 100 can continue to monitor the cardiac signals received by the sensing electrodes 112 to determine whether the patient may be experiencing a cardiac conditions that may require treatment.

Medical Device Operating Modes

In some examples, the external medical device 100 of FIG. 1 can operate in a default mode, a water or shower mode, a patient sleep mode, and/or an activity mode, among others.

Selecting, Entering, and Exiting an Operating Mode

Figure 4B:
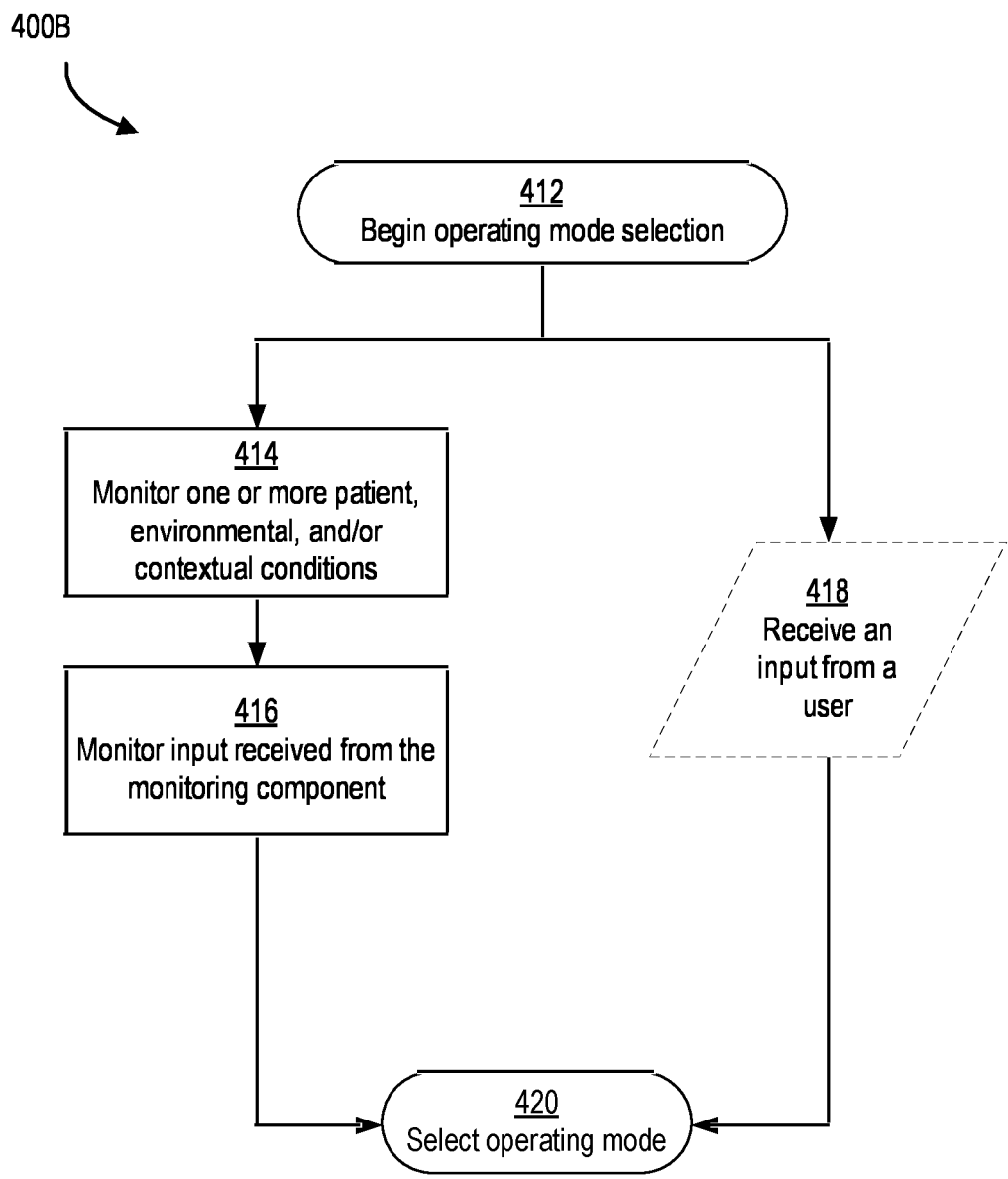
FIG. 4B is an example flow diagram illustrating a methodology for selecting an operating mode of the wearable medical device.

FIG. 4B is a flow diagram 400B illustrating a methodology performed to select an operating mode. The methodology for selecting an operating mode is initiated (block 412). In some implementations, the methodology is initiated by a triggering event, such as upon receiving an input from the user, or some other external event. In some implementations, the methodology for selecting an operating mode is continuously running (e.g., the wearable medical device 100 is continuously in a state in which an operating mode can be selected). The wearable medical device 100 is configured to monitor one or more patient, environmental, and/or contextual conditions (block 414). For example, the wearable medical device 100 can include one or more sensors such as a moisture sensor, a motion sensor (e.g., an accelerometer, a gyroscope, etc.), a pressure sensor (e.g., a strain gauge), and/or a location sensor (e.g., a GPS receiver). The wearable medical device 100 receives signals from the one or more sensors, and the processor 318 processes the signals to ascertain patient, environmental, and/or contextual data (e.g., information related to patient, environmental, and/or contextual conditions.) The wearable medical device 100 also monitors input (e.g., cardiac and/or other patient physiological signals) received from the monitoring component (block 416). The operating mode can then be selected (block 420). The selection may be based at least in part on at least one of i) the one or more patient, environmental, and/or contextual conditions, and ii) the input received from the monitoring component. The selected mode can correspond to a state of the patient being monitored by the wearable medical device 100.

In some implementations, while the device 100 is in a particular operating mode (e.g., a special or non-default operating mode), the device 100 can monitor for one or more patient, environmental, and/or contextual conditions that indicate that the device 100 should return to a default operating mode, or enter another operating mode.

For example, briefly referring to FIG. 7A, a moisture sensor 702 of the wearable medical device 100 may provide a signal to the processor 318 that indicates that the patient is in a humid environment (e.g., in the shower). If the signals received from the moisture sensor 702 indicate a moisture content that meets or transgresses a threshold (e.g., a predetermined threshold), the wearable medical device 100 may enter the water or shower mode. When the signals received from the moisture sensor 702 indicates a moisture content that falls below the threshold (or a second, different predetermined threshold), the device 100 may exit the water or shower mode and return to a default operating mode. In some examples, the device 100 may be configured to automatically switch to the default operating mode after a predetermined amount of time has elapsed. The amount of time that the device 100 remains in a special operating mode can be configured by a user. For example, a user may preconfigure the device 100 to exit the shower or water mode after 30 minutes has elapsed. For example, the patient or other user may be alerted or prompted by the device 100 to provide input confirming that the device 100 should exit the special operating mode and return to the default operating mode. As noted above, the device may also switch to a different special operating mode from a current special operating mode.

In some implementations, the wearable medical device 100 also monitors cardiac signals received by the sensing electrodes 112 and considers such cardiac signals instead of or in addition to the environmental condition data in selecting an operating mode. For example, if the cardiac data indicates that the patient's heart rate is in an elevated state for a predetermined amount of time, then the device may enter the activity mode. For example, the threshold heart rate may be set to 100 beats per minute, and the predetermined amount of time may be set to 120 seconds or 2 minutes. One or more other thresholds and/or times may be possible. In some examples, the threshold and/or time may be user configurable via a user interface (e.g., during initial setup and/or baselining and/or patient fitting).

Other examples of mode selection based on patient, environmental, and/or contextual conditions and/or input received from the monitoring component are described in more detail below with respect to water mode, patient sleep mode, and activity mode, among others.

In some implementations, the user may be prompted to confirm a mode change before the device effects the change in device mode. For example, the device may automatically enter a mode after a predetermined timeout period (e.g., 10-45 seconds, 1-2 minutes, or more) during which a user's response to such a prompt is not received. For example, the predetermined timeout period may be user configurable via a user interface (e.g., during initial setup and/or baselining and/or patient fitting).

In some implementations, the operating mode can be selected based on an input received by the wearable medical device 100 from a user (block 418). For example, a user can manually cause the wearable medical device 100 to enter a particular mode using one or more input mechanisms, such as the touch screen 220 and/or a button on the medical device controller 120 and/or input mechanisms on other components of the wearable medical device (e.g., on the user interface pod 140).

Before, during, and/or after an operating mode is selected, the wearable medical device 100 can continue to monitor the cardiac signals received by the sensing electrodes 112 to determine whether the patient may be experiencing a cardiac conditions that may require treatment. The selected operating mode can determine the particular detection criteria or parameters (e.g., patient parameter conditions) that are used to determine whether the patient may be experiencing a cardiac condition.

In some examples, after the device 100 enters an operating mode, the device 100 may be configured to re-baseline the patient. As previously noted, a treatable condition can be determined based on changes in the heart axis information from a patient normal condition (e.g. baseline values, such as a baseline ECG recording). In this regard, a patient monitored by the medical device can be prompted to carry out a re-baselining process to prepare new ECG templates to be used when the medical device is in the special operating mode. In some implementations, the re-baselining process can occur automatically in response to detecting a change in operating modes. During a re-baselining process, a baseline set of information relating to the patient can be captured as the new set of templates for detecting treatable conditions in the special operating mode.

In some examples, after the device 100 exits an operating mode, the device 100 may be configured to re-baseline the patient. As previously noted, a treatable condition can be determined based on changes in the heart axis information from a patient normal condition (e.g. baseline values, such as a baseline ECG recording). In this regard, a patient monitored by the medical device can be prompted to carry out a re-baselining process to prepare new ECG templates. In some implementations, the re-baselining process can occur automatically in response to detecting a change in operating modes. During a re-baselining process, a baseline set of information relating to the patient can be captured as the new set of templates for detecting treatable conditions in the default operating mode. Additional details concerning a method for baselining patients and determining treatable conditions based on the baselining are disclosed in the '669 patent described above.

Selecting a Treatment Sequence

Figure 5:
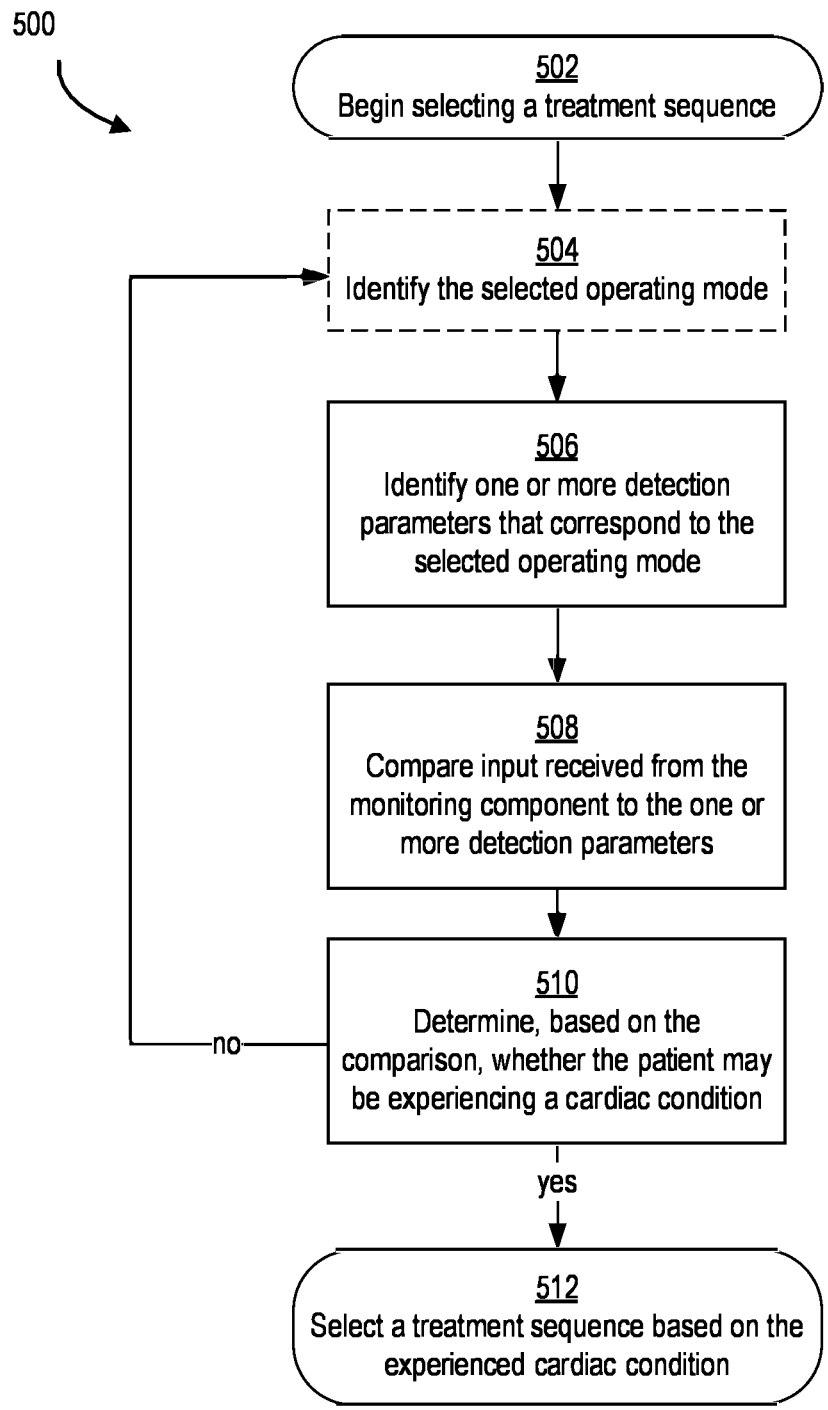
FIG. 5 is an example flow diagram illustrating a methodology for selecting a treatment sequence of the wearable medical device.

FIG. 5 is a flow diagram 500 illustrating a methodology performed to select a treatment sequence. The methodology for selecting a treatment sequence may be initiated (block 502) automatically. For example, the wearable medical device 100 may continuously monitor the cardiac signals received by the sensing electrodes 112 to determine whether the patient may be experiencing a cardiac conditions that may require treatment. Before a special operating mode is selected by the wearable medical device 100, the detection parameters (e.g., conditions) for identifying a cardiac condition may be a default set of parameters. Each special operating mode may be associated with one or more predefined detection parameters. Thus, before determining whether the patient may be experiencing a cardiac condition, the methodology can first identify the selected operating mode (block 504).

The identification of the selected operating mode (block 504) is an optional step. In various implementations, the device 100 may automatically adjust detection parameters in accordance with a predetermined relationship between the detection parameters and the patient, environmental, and/or contextual inputs received from the external sensors. In some examples, rather than dynamically adjusting operating characteristics based on the operating mode, the device 100 may dynamically adjust its operating characteristics in response to the patient, environmental, and/or contextual conditions.

In some implementations (e.g., implementations in which the selected operating mode is identified), one or more detection parameters that correspond to the selected operating mode can be identified (block 506). Inputs received from the monitoring component (e.g., cardiac signals received by the sensing electrodes 112) are then compared to the one or more detection parameters as described above (block 508). Based on the comparison, the wearable medical device 100 then determines whether the patient may be experiencing a cardiac condition (block 510).

Determining whether the patient may be experiencing a cardiac condition (block 510) may include a verification step during which the wearable medical device 100 determines whether the patient's cardiac signals are in fact indicative of a cardiac condition. In some implementations, a cardiac condition may be erroneously identified due to the presence of noise in the cardiac signal (e.g., due to an electrode being partially removed from the patient, due to environmental factors such as wet/humid conditions, etc.). The wearable medical device 100 may analyze a portion of the patient's cardiac signal (e.g., a 20 second ECG portion) and determine whether the cardiac signal represents a noise artifact. The determination may be made according to a machine learning classifier based approach. In some implementations, the cardiac signal is assigned a score, and the score is compared to one or more predetermined cardiac event thresholds. Each cardiac event threshold may correspond to a particular type of cardiac event. For example, one threshold may correspond to a ventricular tachycardia (VT) condition, and another threshold may correspond to a ventricular fibrillation (VF) condition.

Still referring to FIG. 5, if it is determined that the patient is not experiencing a cardiac condition, the wearable medical device 100 may restart the methodology at block 504. In some implementations (e.g., implementations in which the selected operating mode is not identified), the wearable medical device 100 may restart the methodology at block 506. The methodology may continuously step through blocks 504 through 510 (or blocks 506 through 510) so long as a cardiac condition is not detected. If it is determined that the patient may be experiencing a cardiac condition, the wearable medical device selects a treatment sequence based on the experienced cardiac condition (block 512). The particular treatment sequence may be tailored to the patient based on the selected operating mode and the particular cardiac condition that the patient may be experiencing.

Performing a Treatment Sequence

Figure 6:
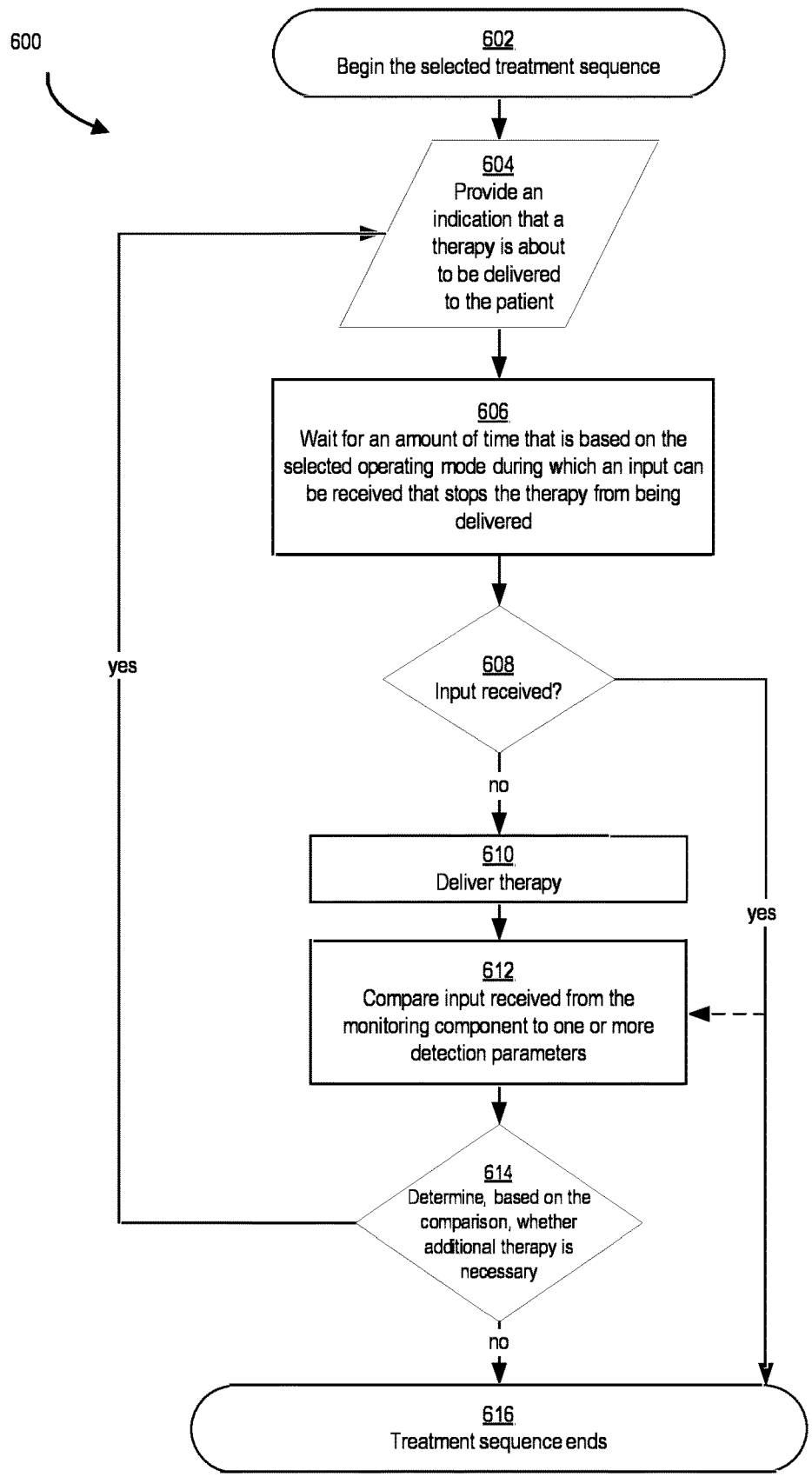
FIG. 6 is an example flow diagram illustrating a methodology for performing the treatment sequence selected according to the methodology illustrated in FIG. 5.

FIG. 6 is a flow diagram 600 illustrating a methodology for performing the selected treatment sequence (e.g., the treatment sequence selected according to the methodology of FIG. 5). The methodology for performing the selected treatment sequence may be initiated (block 602) after the treatment sequence is selected by the wearable medical device 100. In some implementations, the treatment sequence is automatically initiated immediately or substantially immediately after the treatment sequence is selected. Before delivering any therapy, the wearable medical device 100 provides an indication that a therapy is about to be delivered to the patient (block 604). The indication may be audio, visual, haptic, etc. After providing the indication, the wearable medical device 100 waits for an amount of time before delivering the therapy (block 606). In some examples, the length of time (e.g., the length of the delay) can be based on the selected operating mode. For example, the delay may be shorter when the wearable medical device 100 is operating in a default operating mode than the delay that would be applied in a water or shower operating mode. In some implementations, the amount of time is configurable (e.g., by a caregiver, the patient, another user, etc.) via a user interface. For example, an initial configuration may be performed during initial setup and/or baselining.

The length of the delay time before the treatment is delivered may be based at least in part on the particular cardiac condition being experienced, the device operating mode, and/or the particular treatment sequence selected. For example, if the wearable medical device 100 determines that the patient may be experiencing a VT condition (e.g., which may be prone to being misclassified), the patient may be afforded 30 seconds to provide an input to stop the therapy from being delivered. In a water or shower operating mode, the patient may be afforded a longer delay (e.g., 45 seconds) to provide the input. However, if the wearable medical device 100 determines that the patient may be experiencing a VF condition (which, e.g., may be more likely to be immediately life-threatening as compared to a VT condition), the patient may be afforded only 20 seconds to provide the input. In some implementations, in a water or shower mode, the patient may be afforded a longer delay (e.g., 30 seconds) to provide the input.

During the delay time before the treatment is delivered, an input can be received that stops the therapy from being delivered (block 608). For example, the patient can interact with one or both of the response buttons (210 of FIG. 2) to cause the wearable medical device 100 to refrain from delivering the treatment. For example, the treatment may be a "false alarm," such as an unnecessary and/or erroneous treatment suggestion.

In some examples, the input may take a different form depending on the mode of the device. For example, one form of input may be a verbal command issued by the patient (e.g., a spoken phrase such as "STOP TREATMENT" or "SUSPEND TREATMENT"). In some implementation, the device may include voice recognition capability to verify that the patient provided the command and not a bystander. Example methods and systems for using voice recognition to stop and/or suspend a treatment are disclosed in issued U.S. Pat. No. 8,369,944, entitled "Wearable defibrillator with audio input/output," the contents of which are incorporated in their entirety herein. As noted, an ability to provide a verbal command may be available in one or more special modes. For example, in a default mode, the patient may need to provide the input via the response buttons, but in an activity mode, the patient may provide the response via either the response buttons or as a verbal command. One or more other forms of input may be implemented in place of or in addition to either the response buttons or verbal commands. For example, the input received (block 608) can be in the form of patient motion information indicating that the patient is not unconscious. The patient motion information can be combined with other forms of input to confirm the input and stop and/or suspend treatment.

In some implementations, receipt of the input can end the treatment sequence (block 616). However, if no input is received, therapy (e.g., a shock such as a defibrillation shock or a pacing shock) is delivered to the patient (block 610).

After the therapy is delivered, the wearable medical device 100 compares input received from the monitoring component to one or more detection parameters (block 612). For example, input received from the monitoring component can be compared to the same detection parameters described above with reference to block 508 of FIG. 5 for determining whether the patient may be experiencing a cardiac condition. In some implementations, the input received from the monitoring component can be compared to one or more other detection parameters. Based on the comparison, the wearable medical device determines whether additional therapy is necessary (block 614). For example, if the input received from the monitoring component indicates that the patient is experiencing normal heart function, the treatment sequence ends (block 616). On the other hand, if the input received from the monitoring component indicates that the detected cardiac condition persists (or, e.g., that a different cardiac condition exists), the wearable medical device 100 may determine that additional therapy is necessary (block 614) and again provide an indication that a therapy is about to be delivered to the patient (block 604).

In some implementations, receipt of an input (block 608) only temporarily stops the therapy from being delivered to the patient, e.g., rather than ending the treatment sequence altogether (block 616). For example, receipt of the input can stop the therapy from being delivered, but can cause the wearable medical device 100 to compare input received from the monitoring component to one or more detection parameters (block 612) and determine, based on the comparison, whether additional therapy (e.g., additional to the declined therapy) is needed (block 614).

In some implementations, the device 100 can be configured to automatically exit a special operating mode and return to a default operating mode after an initial treatment has been delivered. As such, when the device 100 switches to the default operating mode, the monitoring and/or treatment parameters can be appropriately adjusted for subsequent therapies. In some examples, the device 100 can be configured to exit the special operating mode after the treatment sequence is completed and no further shocks are needed for the patient (e.g., after restoration of normal rhythm). In some implementations, the device 100 can be configured to exit the special operating mode only after the entire treatment sequence is completed.

In some implementations, multiple indications are provided to the patient before a treatment is delivered as described above. The multiple indications may be in various forms. For example, one or more indications may be haptic, and one or more indications may be audible. In some implementations, a first indication is a haptic indication that is intended to attract the patient's attention without disturbing others. In the absence of a response from the patient, the wearable medical device 100 may provide a second indication in the form of a low-volume audible alarm. The second indication may also be intended to attract the patient's attention without causing excessive disturbance to others. If the patient does not respond to the second indication, the wearable medical device 100 may provide a third indication in the form of a loud-volume audible alarm. The third indication may be intended to attract the patient's attention irrespective of whether it may disturb others. In some implementations, the third indication may be intended to attract the attention of others. As described below, the length of time that is afforded to the patient to provide an input may vary according to the mode that the wearable medical device 100 is operating under at the time. Similarly, the lengths and/or number and/or types of indications provided may vary accordingly. For example, in one or more special operating modes, the device 100 may skip the haptic and/or low-volume audible alarms and proceed directly to providing a loud-volume audible alarm. In one or more special operating modes, the device may shorten a duration of a first indication (e.g., haptic alarm) but lengthen durations of one or both of the second indication (e.g., a low-volume alarm) and the third indication (e.g., a loud-volume alarm).

In some implementations, if the wearable medical device 100 initially determines that the patient may be experiencing a cardiac condition but subsequently determines that the supposed cardiac condition is due to a noise artifact in the cardiac signal, the wearable medical device 100 may be configured to modify the treatment sequence. For example, in some implementations, if a noise artifact is detected in the cardiac signal, the wearable medical device 100 may suspend the treatment sequence methodology for a period of time and refrain from providing any indication to the patient. This is sometimes referred to as a silent noise state, which can provide the wearable medical device 100 an opportunity to resolve the erroneous cardiac condition without user interaction. The length of the suspension may be based at least in part on the particular cardiac condition that is supposedly being detected and an operating mode of the device. For example, if the device is in a special operating mode (e.g., water or shower mode or an activity mode), then the length of suspension may be longer than the length of suspension in a default operating mode. For example, if the silent noise state is configured to last about 30 seconds in a default operating mode, the silent noise state can be configured to last about 45 seconds in a special operating mode. The silent noise period can be user configured for each of the default and special operating modes depending on the caregiver and/or patient's preferences. For example, the configuration may be performed in a context of an initial setup and/or baselining and/or patient fitting.

Following the treatment methodology suspension, if the wearable medical device 100 is unable to resolve the erroneous cardiac condition, the wearable medical device 100 may provide an indication that a therapy is about to be delivered. This is sometimes referred to as the noise alarm state, during which the treatment sequence methodology continues to run. If the patient provides an input, the wearable medical device 100 may extend the length of the noise alarm state for a period of time. The extended length of time may be based at least in part on the particular cardiac condition that is supposedly being detected. In some implementations, the patient can provide an indefinite number of inputs to indefinitely extend the noise alarm state.

Special Medical Device Operating Modes

As described above, the wearable medical device 100 can operate in a default operating mode and one or more of a plurality of special operating modes. For example, the wearable medical device 100 can operate in a water mode (sometimes referred to as a shower mode), a patient sleep mode, and/or an activity mode, among others. The operating mode that the wearable medical device 100 is in can substantially influence its detection, alarms/alerts, and treatment sequences as described above.

Water Operating Mode

FIG. 7A shows an example of the wearable medical device 100 being used in the shower. In this example, the wearable medical device 100 is in water mode (e.g., shower mode). The wearable medical device 100 includes a moisture sensor 702 that is configured to provide signals indicative of an environmental humidity to the processor 318. The wearable medical device 100 also includes an audio interface component 704 that can include one or both of a speaker and a microphone, the functions of which are described in more detail below.

Selecting the Water Operating Mode

Figure 7B:
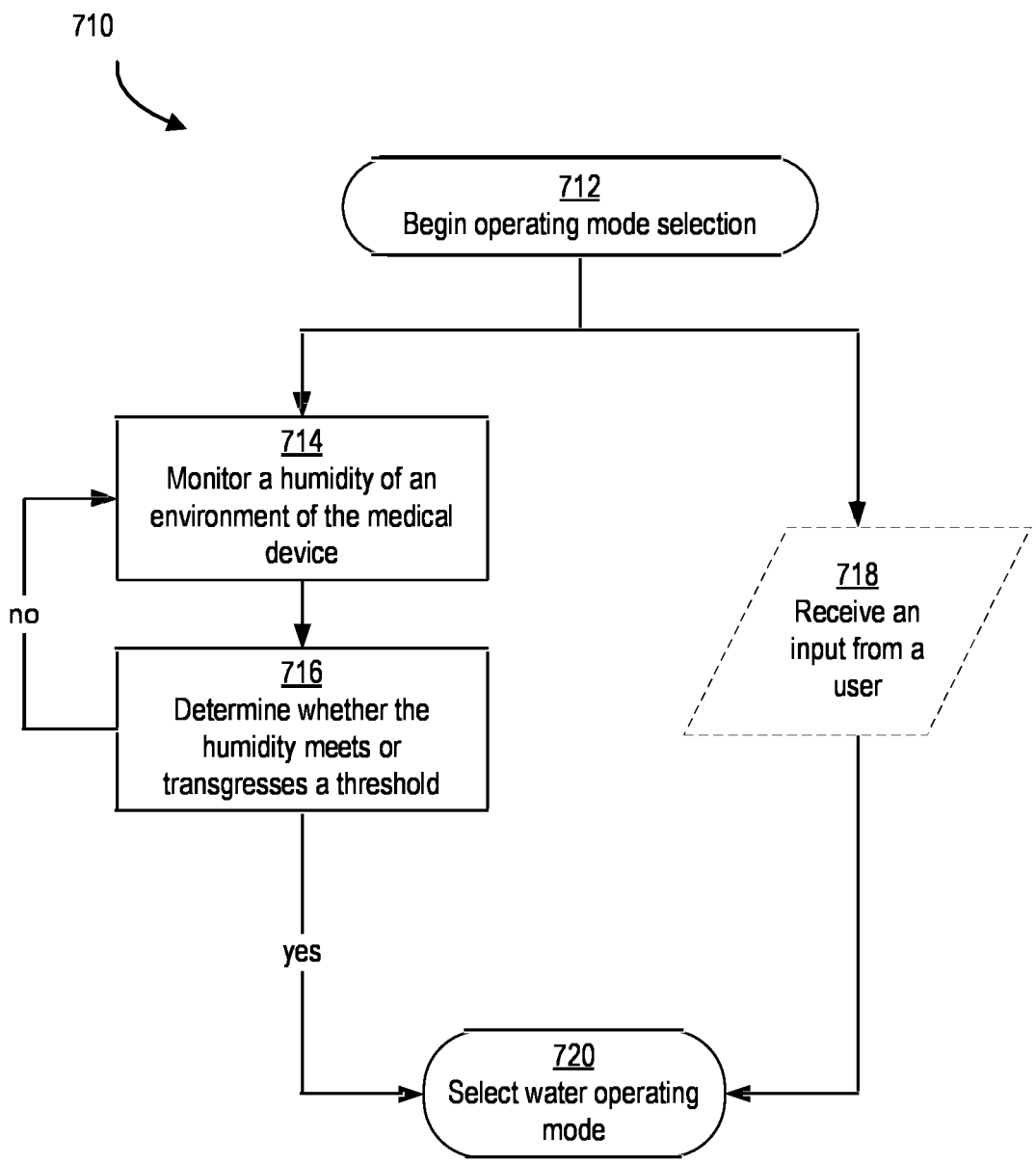
FIG. 7B is an example flow diagram illustrating a methodology for selecting the water operating mode of the wearable medical device.

The wearable medical device 100 may have entered the water mode based on a methodology illustrated in a flow diagram 710 of FIG. 7B. The methodology for selecting an operating mode is initiated (block 712) (e.g., automatically or in response to a triggering event). For example, the methodology for selecting an operating mode may be continuously running, or the methodology may initiate upon receiving an input from a user. The wearable medical device 100 is configured to monitor one or more environmental conditions, including a humidity of an environment of the wearable medical device 100 (block 714). For example, the moisture sensor 702 can provide signals to the processor 318 indicative of the environmental humidity. The wearable medical device 100 then determines whether the humidity meets or exceeds a threshold (e.g., a predetermined threshold). If the humidity does not meet nor exceed the threshold, the wearable medical device 100 may continue to monitor the humidity (block 714). The monitoring may continue indefinitely or for a fixed period of time (e.g., in the order of minutes, hours, or even longer). In some implementations, the wearable medical device 100 may continue to monitor other environmental conditions to determine whether a different operation mode (e.g., other than the water mode) should be selected. If the humidity meets or exceeds the threshold, the water operating mode is selected 720.

In some examples, a microphone can be employed instead of or in addition to the moisture sensor 702. The microphone can be configured to detect the sound of falling water. Signals from such a microphone can be used to correlate and/or confirm the information from the moisture sensor 702.

In some implementations, the water operating mode can be selected based on an input received by the wearable medical device 100 from a user (block 718). For example, a user can manually cause the wearable medical device 100 to enter a particular mode using one or more input mechanisms, such as the touch screen 220 and/or a button on the medical device controller 120 and/or input mechanisms on other components of the wearable medical device (e.g., the user interface pod 140).

Selecting a Treatment Sequence in the Water Operating Mode

Figure 7C:
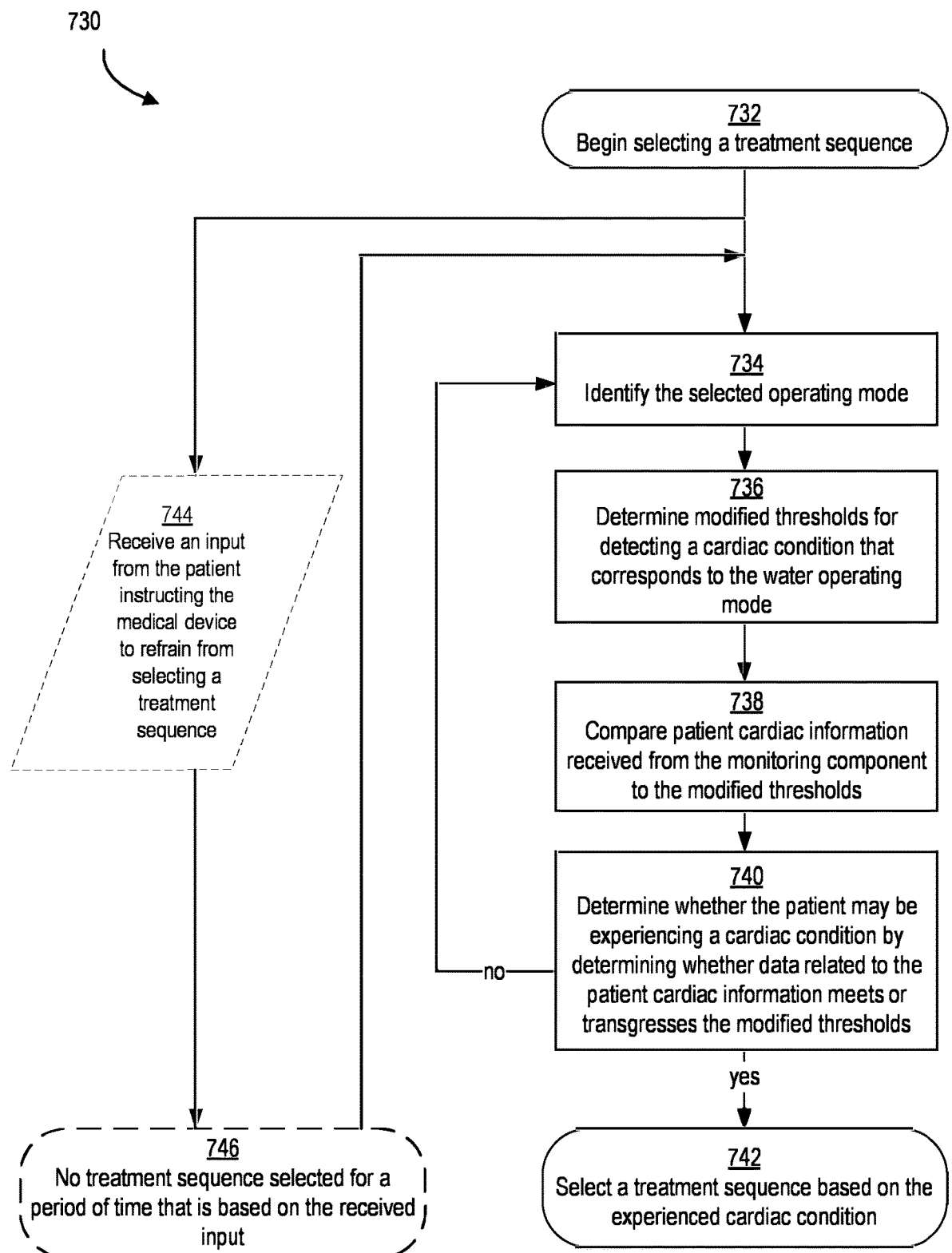
FIG. 7C is an example flow diagram illustrating a methodology for selecting a treatment sequence of the wearable medical device.

While in the water operating mode, the wearable medical device 100 can monitor the cardiac signals received by the sensing electrodes 112 and determine whether the patient may be experiencing a cardiac condition that may require treatment based on modified detection parameters. As noted, the particular detection conditions that are used to determine whether a cardiac condition is present may be based at least in part on the water operating mode. For example, FIG. 7C is a flow diagram 730 that illustrates a methodology performed by the wearable medical device 100 to select a treatment sequence. The methodology for selecting a treatment sequence may be initiated (block 732) automatically. In other words, the wearable medical device may continuously monitor the cardiac signals to determine whether a cardiac condition exists. The wearable medical device 100 then identifies the selected operating mode (block 734), which in this example is the water operating mode.

As mentioned above, the detection parameters (e.g., conditions) for identifying a cardiac condition in a special operating mode may be different than those used in the default operating mode. Once it is determined that the water operating mode is currently selected, the wearable medical device 100 determines modified thresholds for detecting whether a cardiac condition exists in the patient (block 736).

As noted above, the modified thresholds for the special operating mode can be preset during an initial fitting and/or baselining state. In some examples, the modified thresholds for the special operating mode can be preset before the device is shipped to the patient service representative or caregiver for fitting on a patient.

For example, the modified thresholds for the water mode can include one or more of modified phase detection parameters, modified magnitude detection parameters, and/or modified noise detection parameters (e.g., an ECG score and/or an amount of time for the device to declare a VT/VF event, as described above). For example, for the water mode, the modified ECG score threshold can be set to 12. For example, the modified parameters can include modified thresholds that if met of transgressed can cause the device to take action as described herein.

The modified thresholds correspond to the water operating mode and may have the effect of reducing the sensitivity of the wearable medical device 100. While in the shower or taking a bath, a patient may lift or cause excessive movement of the ECG sensors. The excessive motion of the patient and/or the sensors can cause noise artifacts that are sometimes significant. In some examples, the noise artifacts can result in false alerts and/or alarms that can be annoying or concerning to the patient. Thus, in the water mode, the device can be configured to ride through the noisy events. The patient's cardiac information that is received from the monitoring component is compared to the modified thresholds (block 738) as described in detail above. In some implementations, only one parameter is modified in the water mode relative to the default mode. In some implementations, one or more of phase detection parameters, magnitude detection parameters, and/or noise detection parameters can be modified. For example, in the water mode, the cardiac detection analyzer may use one or more modified phase detection parameters and modified magnitude detection parameters. Further, in some examples, the noise detection module can compare an ECG score derived as described above to a modified ECG score threshold.

The wearable medical device 100 then determines whether the patient may be experiencing a cardiac condition by determining whether data related to the patient cardiac information meets or transgresses the modified thresholds (block 740). For example, continuing the example above, a cardiac condition may exist if the methodology, using the modified phase and magnitude detection parameters, determines that an incoming ECG signal does not match baseline ECG measurements within a predetermined period of time. Further, the noise detection methodology described above can confirm the cardiac condition on the basis of the modified ECG score threshold.

If the methodology determines that the patient may be experiencing a cardiac condition, an appropriate treatment sequence is selected based on the particular cardiac condition (block 742). However, if it is determined that the patient is not experiencing a cardiac condition, the methodology may revert to identifying the selected operating mode (block 734) (e.g., in case it has changed since the previous identification) and proceed according to the methodology shown.

In some implementations, the wearable medical device 100 can be instructed to refrain from selecting a treatment sequence. For example, the wearable medical device 100 can be configured to receive an input from the patient that instructs the medical device to refrain from selecting a treatment sequence (block 744). The input may be provided in response to an indication that treatment sequence selection has been initiated. In response to the input, the wearable medical device 100 may refrain from selecting a treatment sequence for a period of time (block 746), in some examples acting as a snooze function. The period of time may be based on the particular input received. The period of time can be indefinite or fixed (e.g., in the order of minutes, hours, or even longer). Following the period of time, the methodology may proceed to identifying the selected operating mode (block 734) and proceed according to the methodology shown.

Performing a Treatment Sequence in the Water Operating Mode

Figure 7D:
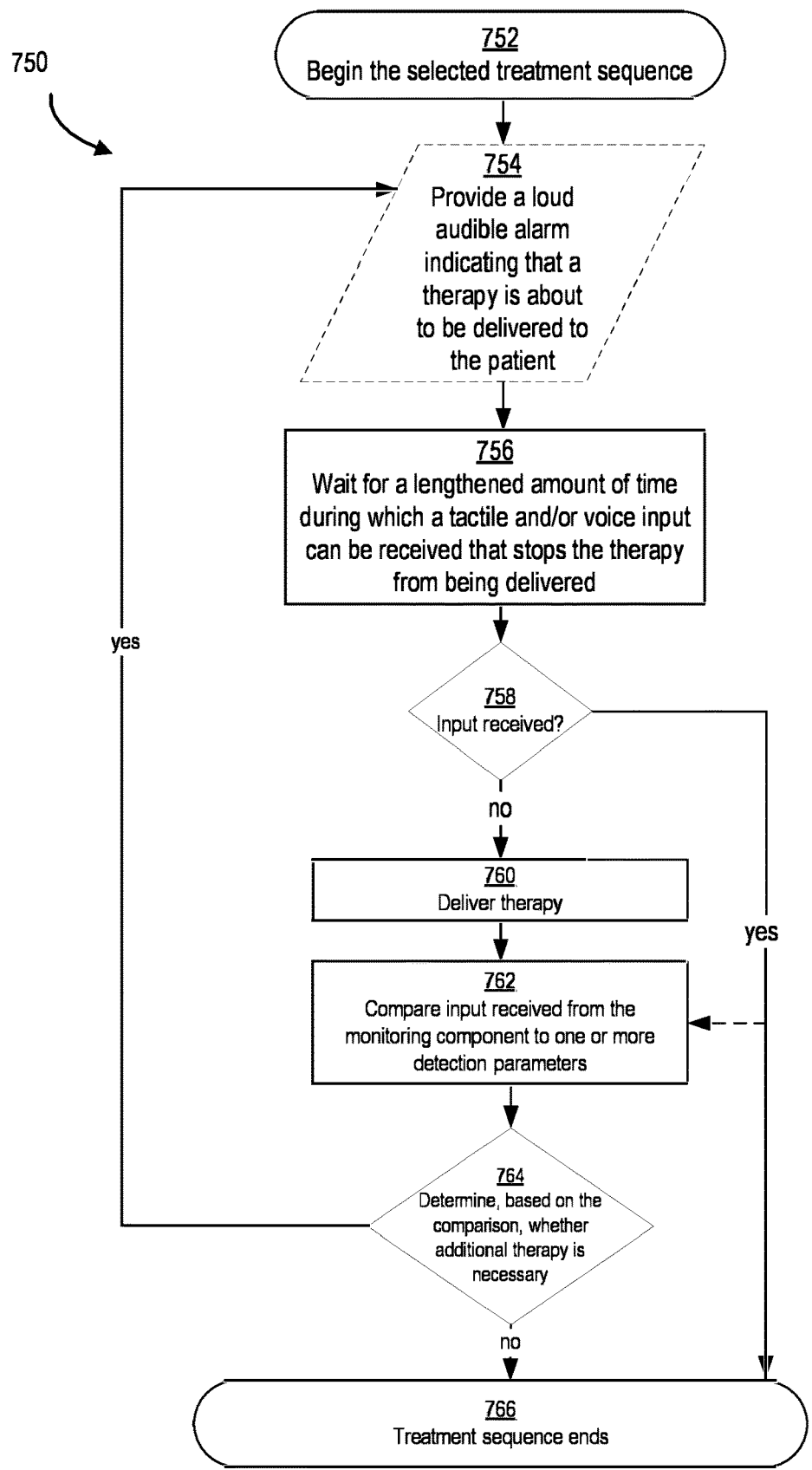
FIG. 7D is an example flow diagram illustrating a methodology for performing the treatment sequence selected according to the methodology illustrated in FIG. 7C.

FIG. 7D is a flow diagram 750 illustrating a methodology for performing the selected treatment sequence (e.g., the treatment sequence selected according to the methodology of FIG. 7C). After the methodology is initiated (block 752), the wearable medical device 100 may provide an indication that a therapy is about to be delivered to the patient (block 754). The indication may be based on the operating mode that the wearable medical device 100 is operating under at the time (in this example, the water mode). As mentioned above, the water mode may be selected when the patient is in the shower. Because showers produce a high volume of noise, the indication can be in the form of an alarm (e.g., that is emitted by a speaker of the audio interface component 704 of FIG. 7A) having a sufficient volume such that it can be heard by the patient. In some implementations, the wearable medical device 100 includes a microphone for receiving an audio input. The volume of the alarm can be determined based on a magnitude of noise of the audio input. Before delivering the therapy, the wearable medical device waits for a length of time during which an input can be received that stops the therapy from being delivered (block 756). The length of time and/or the particular way that the input can be received can be tailored to the water operating mode. For example, because a patient who is showering may be preoccupied, or because false alarms in water mode may be prevalent (e.g., due to the patient temporarily removing one or more of the electrodes), the length of time may be longer than a default length of time to allow the patient a sufficient opportunity to stop an unnecessary treatment from being delivered. Similarly, additional types of inputs can be accepted by the wearable medical device 100 when it is in water mode to assist the user. For example, the microphone can be configured to receive an audio input from the user. In some examples, a portion of the wearable medical device 100 may remain outside of the shower, making it difficult for the patient to provide a tactile input (e.g., press one or both of the response buttons 210). Thus, configurations that allow for audio input can make it easier for the patient to stop the treatment from being delivered.

During the length of time, the methodology determines whether an input is received (block 758). If an input is received, the treatment sequence may end (block 766). However, if no input is received, the therapy is delivered to the patient (block 760). After the therapy is delivered, the wearable medical device 100 compares input received from the monitoring component to one or more detection parameters (block 762). For example, input received from the monitoring component (e.g., patient cardiac signals) can be compared to the threshold described above with reference to block 738 of FIG. 7C for determining whether the patient may be experiencing a cardiac condition. In some implementations, the input received from the monitoring component can be compared to one or more other detection parameters. Based on the comparison, the wearable medical device determines whether additional therapy is necessary (block 764). For example, if the input received from the monitoring component indicates that the patient is experiencing normal heart function, the treatment sequence ends (block 766). On the other hand, if the input received from the monitoring component indicates that the detected cardiac condition persists (or, e.g., that a different cardiac condition exists), the wearable medical device 100 may determine that additional therapy is necessary and again provide a loud audible alarm indicating that a therapy is about to be delivered to the patient (block 754).

In some implementations, receipt of an input (block 758) only temporarily stops the therapy from being delivered to the patient (e.g., rather than ending the treatment sequence altogether (block 766)). For example, receipt of the input can stop the therapy from being delivered, but can cause the wearable medical device 100 to compare input received from the monitoring component to one or more detection parameters (block 762) and determine, based on the comparison, whether additional therapy (e.g., additional to the declined therapy) is needed (block 764).

Patient Sleep Operating Mode

Figure 8:
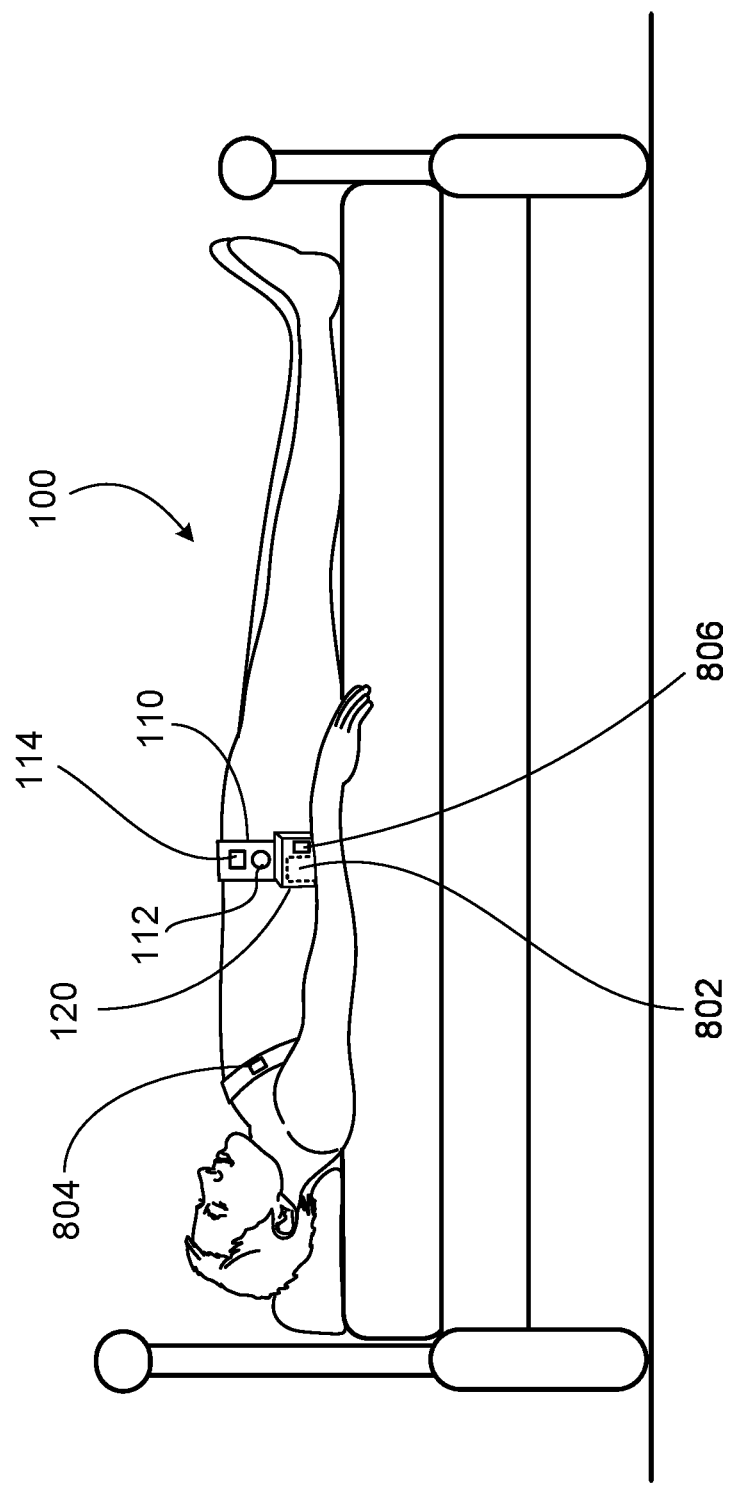
FIG. 8 shows an example of the wearable medical device being used while a patient is sleeping.

FIG. 8 shows an example of the wearable medical device 100 being used while the patient is sleeping. In this example, the device 100 is in a patient sleep operating mode. The wearable medical device 100 includes a pressure sensor 802 (e.g., a strain gauge) that is configured to provide signals indicative of a degree of pressure to the processor 318, and a motion sensor 806 that is configured to provide signals indicative of a degree of motion to the processor 318. The wearable medical device 100 also includes a vibration motor 804.

Selecting the Patient Sleep Operating Mode

The wearable medical device 100 may have entered the patient sleep operating mode based on a methodology similar to that described above with reference to FIG. 4B. For example, the patient may provide an input to manually enter the device into the patient sleep operating mode (see step 418 of FIG. 4B).

In some examples, the wearable medical device 100 is configured to monitor one or more environmental conditions. For example, the environmental conditions include a degree of pressure and a degree of motion experienced by the wearable medical device 100.

The pressure sensor 802 (e.g., which can be incorporated on a posterior of the garment 110) can include a strain gauge that includes a strain sensitive metal foil pattern. When pressure is applied to certain portions of the wearable medical device 100, the metal foil deforms. The deformation causes the overall length of the metal foil pattern to change. The physical change in the metal foil pattern causes the end-to-end electrical resistance of the pattern to change. An output voltage across terminals of the metal foil pattern corresponds to the change of resistance, and therefore is indicative of an amount of strain measured by the strain gauge. The pressure sensor 802 can provide information related to the amount of strain to the processor 318, and the processor 318 can determine whether the amount of strain meets or exceeds a predetermined threshold. The threshold may be indicative of a degree of pressure typically experienced when the patient is sitting or lying down.

The motion sensor 806 can include one or more accelerometers, gyroscopes, or other kinds of sensors that are configured to measure motion and/or orientation information and provide such information to the processor 318. The processor can determine whether the motion and/or orientation information is below a predetermined threshold. The threshold may be indicative of a degree of motion typically experienced when the patient is in a non-sleep state.

The wearable medical device 100 can consider one or both of the pressure information and the motion information to determine whether the patient sleep operating mode should be selected. For example, if the strain threshold is met or exceeded and/or the motion information is below the threshold, the wearable medical device 100 may infer that the patient is lying down and/or sitting down, and may enter the patient sleep operating mode accordingly. In some implementations, a user who is sitting or lying down is not necessarily asleep. Thus, in some implementations, the wearable medical device 100 can consider other information instead of or in addition to the pressure and motion information to determine whether the patient sleep operating mode should be selected. For example, the wearable medical device 100 may consider input (e.g., patient cardiac signals) received from the monitoring component and/or other patient health metrics (e.g., a heart rate below a threshold) to determine whether the patient is exhibiting a condition typically associated with sleep.

Selecting a Treatment Sequence in the Patient Sleep Operating Mode

The methodology for selecting a treatment sequence when the wearable medical device 100 is in the patient sleep operating mode may be similar to the methodology described above with reference to FIG. 5. The particular conditions that are used to determine whether the patient may be experiencing a cardiac condition may be based at least in part on the default operating mode.

In some examples, a patient who is sleeping may exhibit different cardiac signals than those typically exhibited while awake. Thus, the conditions for determining whether a cardiac condition exists may be different when the patient is sleeping. For example, the wearable medical device 100 may implement a lessened threshold for detecting whether a cardiac condition exists, thereby having the effect of increasing the sensitivity of the wearable medical device 100.

In some implementations, the wearable medical device 100 may be configured to detect other medical conditions of the patient (e.g., in addition to cardiac conditions) based on the operating mode. For example, while in the patient sleep operating mode, the wearable medical device 100 may be configured to initiate its ability to detect sleep apnea in the patient. Indicators of sleep apnea may be related to transthoracic impedance, respiration rate, heart rate, certain pulmonary and/or heart sounds, and pulse oximetry, among others. The wearable medical device 100 can include one or more sensors configured to monitor one or more of these indicators to determine whether the patient is experiencing sleep apnea. In some implementations, the wearable medical device 100 is configured to alert the patient (e.g., with an audible and/or haptic alarm) if sleep apnea is detected. In some implementation, the detection of sleep apnea may indicate that the patient is experiencing a cardiac condition. Thus, in some implementations, a patient who is experiencing symptoms of sleep apnea, but who is not exhibiting other specific signs of a cardiac condition, may be treated as potentially experiencing a cardiac condition. In some implementations, the wearable medical device 100 may be configured to proceed with selecting a treatment sequence based on characteristics of the sleep apnea.

Performing a Treatment Sequence in the Patient Sleep Operating Mode

The methodology for performing a treatment sequence when the wearable medical device 100 is in the patient sleep operating mode may be similar to the methodology described above with reference to FIG. 6. The way by which the wearable medical device 100 provides an indication that a therapy is about to be delivered may be based at least in part on the patient sleep operating mode. For example, the indication can be a haptic indication provided by the vibration motor 804 so as not to alarm the patient and/or disturb other individuals who are sleeping in the vicinity of the patient. In some examples, the indication can be an audible alarm provided by a speaker that is intended to awaken the patient. In some examples, the intensity of the indication (e.g., the vibration intensity, the volume, etc.) can be adjustable such that the patient can define an intensity that is sufficient to awaken him or her.

The way by which the patient can provide an input to stop the therapy from being delivered may be based at least in part on the patient sleep operating mode. The patient may be in a disoriented state upon awakening in response to the indication. The wearable medical device 100 may be configured to receive inputs other than tactile inputs (e.g., pressing one or both of the response buttons 210), such as an audio input that can be received by a microphone, thereby allowing the patient to more easily stop the therapy from being delivered.

The length of time afforded to the patient to provide the input may be based at least in part on the patient sleep operating mode. The patient may have trouble waking up, or may be in a disoriented state upon awakening in response to the indication. The treatment sequence may be adjusted such that the patient is afforded more time to provide an input than the amount of time afforded in the default operating mode. For example, the patient may be afforded 45 seconds to provide an input before the therapy is delivered.

Activity Operating Mode

Figure 9:
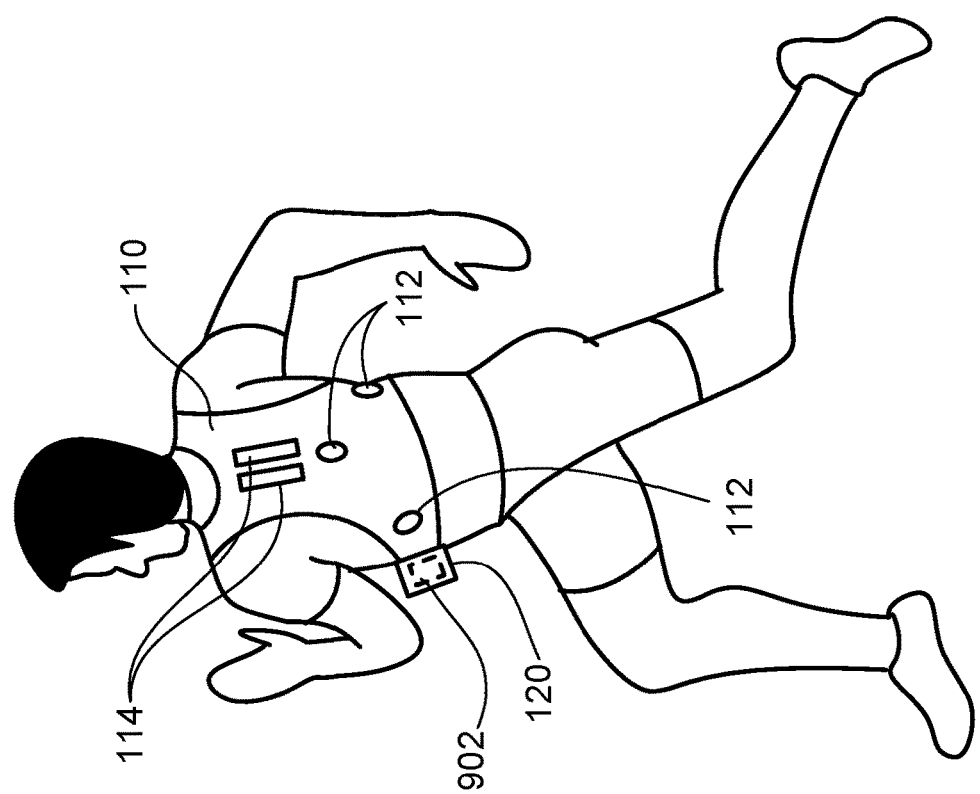
FIG. 9 shows an example of the wearable medical device being used while the patient is active.

FIG. 9 shows an example of the wearable medical device 100 being used while the patient is active. In this example, the device is in an activity operating mode. The wearable medical device 100 includes a motion sensor 902 that is configured to provide signals indicative of a degree of motion to the processor 318. The motion sensor 902 can include one or more accelerometers and/or gyroscopes that are configured to measure motion and/or orientation information.

Selecting the Activity Operating Mode

The wearable medical device 100 may have entered the activity operating mode based on a methodology similar to that described above with reference to FIG. 4B. For example, the patient may provide input to place the device 100 in the activity operating mode (see step 418 of FIG. 4B). In some implementations, the wearable medical device 100 is configured to monitor one or more environmental conditions. In some implementations, the environmental conditions include a degree of motion experienced by the wearable medical device 100. The motion sensor 806 can include one or more accelerometers and/or gyroscopes that are configured to measure motion and/or orientation information and provide such information to the processor 318. The processor 318 can determine whether the motion and/or orientation information is above a predetermined threshold. The threshold may be indicative of a degree of motion typically experienced when the patient is in an active state.

The wearable medical device 100 can consider the motion information to determine whether the activity operating mode should be selected. For example, if the motion threshold is met or exceeded, the wearable medical device 100 may infer that the patient is in an active state, and may enter the activity operating mode accordingly. In some implementations, the wearable medical device 100 can consider other information instead of or in addition to the motion information to determine whether the activity operating mode should be selected. For example, the wearable medical device 100 may consider input (e.g., patient cardiac signals) received from the monitoring component and/or other patient health metrics (e.g., a heart rate and/or a respiratory rate above a threshold) to determine whether the patient is exhibiting a condition typically associated with activity.

Selecting a Treatment Sequence in the Activity Operating Mode

The methodology for selecting a treatment sequence when the wearable medical device 100 is in the activity operating mode may be similar to the methodology described above with reference to FIG. 5. The particular conditions that are used to determine whether the patient may be experiencing a cardiac condition may be based at least in part on the activity operating mode and may be adjusted relative to default conditions. In some cases, a patient who is active may exhibit different cardiac signals than those typically exhibited while inactive. Thus, the conditions for determining whether a cardiac condition exists may be different when the patient is active (e.g., playing a sport).

The modified thresholds correspond to the activity operating mode and may have the effect of reducing the sensitivity of the wearable medical device 100. While playing a sport and/or running and/or otherwise being active, a patient may unintentional lift or cause excessive movement of the ECG sensors. The excessive motion of the patient and/or the sensors can cause noise artifacts that are sometimes significant. In some examples, the noise artifacts can result in false alerts and/or alarms that can be annoying or concerning to the patient. Thus, in the activity mode, the device can be configured to ride through the noisy events. The patient's cardiac information that is received from the monitoring component is compared to the modified thresholds (block 738) as described in detail above.

In some implementations, only one parameter is modified in the activity mode relative to the default mode. In some implementations, one or more of phase detection parameters, magnitude detection parameters, and/or noise detection parameters can be modified. For example, in the activity mode, the cardiac detection analyzer may use one or more modified phase detection parameters and modified magnitude detection parameters. Further, in some examples, the noise detection module can compare an ECG score derived as described above to a modified ECG score threshold.

Performing a Treatment Sequence in the Activity Operating Mode

The methodology for performing a treatment sequence when the wearable medical device 100 is in the activity operating mode may be similar to the methodology described above with reference to FIG. 6. The way by which the wearable medical device 100 provides an indication that a therapy is about to be delivered may be based at least in part on the activity operating mode. For example, after the treatment methodology is initiated, the wearable medical device 100 may provide an indication that a therapy is about to be delivered to the patient. The indication may be based on the activity operating mode that the wearable medical device 100 is operating under.

As mentioned above, the activity mode may be selected when the patient is in the performing a sport or other physical activity. Because such activities can produce a high volume of audible noise, the indication can be in the form of an alarm (e.g., that is emitted by a speaker of the audio interface component 704 of FIG. 7A) having a sufficient volume such that it can be heard by the patient. In some implementations, the wearable medical device 100 includes a microphone for receiving audio input. The volume of the alarm can be determined based on a magnitude of noise of the audio input. Before delivering the therapy, the wearable medical device waits for a length of time during which an input can be received that stops the therapy from being delivered. The length of time and/or the particular way that the input can be received can be tailored to the activity operating mode. For example, because a patient who is performing an activity may be preoccupied, or because false alarms in activity mode may be prevalent (e.g., due to the patient temporarily removing one or more of the electrodes), the length of time may be longer than a default length of time to allow the patient a sufficient opportunity to stop an unnecessary treatment from being delivered.

The way by which the patient can provide an input to stop the therapy from being delivered may be based at least in part on the activity operating mode. For example, the ability of the patient to suspend a treatment via a spoken command may be initiated in the activity mode. As such, additional types of inputs can be accepted by the wearable medical device 100 when it is in activity mode to assist the user. For example, the microphone can be configured to receive an audio input from the user. In some examples, it may be difficult for the patient to provide a tactile input (e.g., by pressing one or both of the response buttons 210) while the patient is performing a physical activity. Thus, configurations that allow for audio input can make it easier for the patient to stop the treatment from being delivered. If an input is received, the treatment sequence may be suspended. However, if no input is received, the therapy is delivered to the patient.

The length of time afforded to the patient to provide the input may be based at least in part on the activity operating mode. In some implementations, the patient may be preoccupied or distracted in the active state. The treatment sequence may be adjusted such that the patient is afforded more time to provide an input than the amount of time afforded in the default operating mode. For example, the patient may be afforded 45 seconds to provide an input before the therapy is delivered. However, in some implementations, the patient may be more susceptible to a cardiac condition while in the active state. For example, an elderly patient or a patient with a particular cardiac health history may be at risk when he or she is active. The treatment sequence may be adjusted such that potentially life threatening cardiac conditions are treated without excessive delay. For example, the patient may be afforded less time to provide an input than the amount of time afforded in the default operating mode. For example, the patient may be afforded 20 seconds to provide an input before the therapy is delivered.

Medical Device Learning

In some implementations, the wearable medical device 100 is configured to acquire data related to its pattern of use, including locations visited, conditions experienced, treatments applied, and situations encountered, among others. The wearable medical device 100 can use such pattern of use data to learn how the wearable medical device 100 has been used in the past, and to assist in setting operational parameters for future uses. In some implementations, the pattern of use data can assist in selecting an operating mode and selecting and/or performing a treatment sequence. The data related to the pattern of use may be acquired automatically (e.g., during the first day or week of use by the patient) or manually (e.g., in response to input received by the user).

Selecting the Operating Mode

In some implementations, the wearable medical device 100 includes a location module that is configured to measure the location of the medical device. The location module may be one or more of a GPS module, an NFC module, a Bluetooth® module, a WLAN module, or one or more indoor positioning systems (IPS) that are configured to provide a signal to the processor 318 indicative of the location of the patient outfitted with the wearable medical device 100. The location may be in the form of GPS coordinates or some other coordinate system (e.g., coordinates associated with an indoor positioning system). In some implementations, the location is correlated with additional information to determine characteristics of the location. For example, the location may be correlated with a database (e.g., a mapping database) to determine that a particular location corresponds to a restaurant, a gym, an athletic facility, a park, a hotel, etc. The characteristics of the location can assist in automatic operating mode selection. For example, the wearable medical device 100 may enter the activity operating mode when the patient is at a location that corresponds to a gym or an athletic facility.

The wearable medical device 100 can identify its location when it is in a particular operating mode. Over time, the wearable medical device 100 can correlate particular locations with particular operating modes. For example, the wearable medical device 100 may recognize that it operates in patient sleep operating mode whenever it is at a location associated with the patient's bedroom. Once the correlation is sufficiently established, the wearable medical device 100 may automatically enter patient sleep operating mode when the patient is in that bedroom. In some implementations, the wearable medical device 100 may wait for a particular period of time before automatically entering the particular operating mode. For example, continuing with the previous example, the wearable medical device 100 may wait five minutes after the patient enters the bedroom before entering the patient sleep operating mode to account for situations in which the patient is briefly in the bedroom for non-sleep reasons.

In some implementations, the wearable medical device 100 can identify patterns of use unrelated to the location of the device to assist in operating mode selection. For example, the wearable medical device 100 may identify that it typically enters the water operating mode on weekdays at 7:00 AM. If a correlation between the operating mode and such patterns is sufficiently established, the wearable medical device 100 may automatically enter the water operating mode at times that fit within the established pattern. In some implementations, rather than automatically entering the particular operating mode, the wearable medical device may "expect" to enter the operating mode, and thus may relax threshold conditions for entering the operating mode during particular time periods.

In some implementations, the patient can manually enter information related to operating mode correlations into the wearable medical device 100. For example, when the patient is at the gym, he or she may instruct the wearable medical device 100 to automatically enter activity operating mode whenever the patient is at the location associated with the gym. The instruction may be provided using a pulldown menu or some other configuration presented by a user interface (e.g., the touch screen 220) or input mechanism.

Selecting/Performing a Treatment Sequence

Pattern of use data can also be used to assist in selecting and/or performing a treatment sequence. As described above, the wearable medical device 100 is configured to compare patient information to detection parameters to determine whether the patient is experiencing a cardiac condition, select a treatment sequence based on the experienced cardiac condition, and provide the treatment sequence. The patient can stop the treatment from being delivered by providing an input to the wearable medical device 100. In some implementations, the wearable medical device 100 can store information related to such overridden treatments to better refine the detection parameters. For example, if the patient always refuses a treatment that is suggested based on a particular detection parameter, a threshold related to that detection parameter may be heightened or lowered accordingly (e.g., to reduce the sensitivity of the wearable medical device with respect to the detection parameter).

Alternative Implementations

While certain implementations have been described, other implementations are possible.

While the medical device has been described as being configured to operate in a default mode and various special operating modes (e.g., water mode, patient sleep mode, activity mode), in some implementations, the medical device is configured to operate in additional modes. The additional modes can include an acrobatic operating mode for when the patient is performing acrobatics and/or a physical intimacy operating mode for when the patient is engaging in physical intimacy. In some implementations the acrobatic operating mode and the physical intimacy operating mode can follow a methodology similar to that described with reference to the activity operating mode. A patient engaging in acrobatics and/or physical intimacy may exhibit different cardiac signals than those typically exhibited while inactive. Thus, in some implementations, the acrobatic operating mode and/or the physical intimacy mode may cause the medical device to implement modified thresholds for detecting whether a cardiac condition exists in the patient, thereby having the effect of decreasing the sensitivity of the medical device. The amount of time afforded to the patient to provide an input to stop the therapy from being delivered may also be adjusted in these modes (e.g., the amount of time may be increased, or in some implementations, decreased).

The plurality of operating modes can each include additional features beyond those described above. Such additional features are sometimes referred to herein as sub-modes. The sub-modes can include noisy mode, home mode, motor vehicle mode, car mode, motorcycle mode, physical impairment mode, and muffled mode. Like the special modes described above, the sub-modes may cause the medical device to adjust its methodology for selecting a treatment sequence and/or adjust its methodology for performing the treatment sequence. For example, the medical device may enter noisy mode if it detects ambient noise of a magnitude beyond a threshold, and the treatment sequence may be modified such that a haptic indication is provided for notifying the patient that a treatment is about to be delivered. Alternatively, the indication may be an audible alert that is sufficient in volume to be heard over the ambient noise. In some implementations, the medical device may enter a motor vehicle mode (e.g., a car mode and/or a motorcycle mode) in which an audio interface of the medical device is configured to receive and provide audible information. The audio interface can be configured to interact with a car audio system.

In some implementations, the medical device can be configured to adjust its user interface arrangement and/or its method of reporting information based on a sub-mode. For example, in some implementations, the sub-modes can include medical facility mode, tech support mode, paramedic/EMS mode, and pediatric mode.

For example, in medical facility mode, the medical device may provide two types of information: basic information that is provided to the patient, and complex information that is provided to a caregiver.

In paramedic/EMS mode, the medical device may provide information to a paramedic and/or allow the paramedic to control at least some aspects of the medical device. For example, in paramedic/EMS mode, a paramedic may be able to adjust treatment parameters for determining whether the patient may be experiencing a medical condition. In some implementations, the paramedic/EMS mode may be entered in response to the medical device detecting a noise signature of an ambulance siren.

In pediatric mode, the medical device may provide alerts in a style that is tailored towards kids (e.g., displaying cartoons on the device) and concurrently provide more detailed alerts to another entity (e.g., a parent).

In tech support mode, the medical device may be configured to provide troubleshooting information related to the medical device to a technical user. In some implementation, one or more of these sub-modes can also cause the medical device to adjust the treatment sequence and/or the detection parameters for determining whether the patient is experiencing a cardiac event.

One or more parameters corresponding to these modes can be adjusted (e.g., during initial patient fitting and/or baselining).

As described above, the medical device determines whether the patient may be experiencing a cardiac condition based on one or more detection parameters (e.g., conditions), and such detection parameters may depend on the mode that the medical device is operating under at the time. One example of a detection parameter that is described above is related to the power spectral density (PSD) of a cardiac signal (e.g., an ECG signal). However, other detection parameters can be used instead of or in addition to the PSD. For example, one or more of the detection parameters can be related to other components of the patient's ECG signal, such as waveform shape variations (e.g., QRS shape), duration variations (e.g., QRS or T-wave width, ST segment width), amplitude variations (e.g., R wave or T-wave amplitude), period variations (e.g., R-R interval, QT interval, ST interval), T wave alternans (TWA), heart rate variability (HRV), heart rate turbulence (HRT), PR interval, slurring of the QRS complex, premature ventricular contraction (PVC), frequency analysis, a VT or VF template, QT variability, QT interval length, and/or combinations and/or ratios of the aforementioned.

While we have described the medical device as being configured to measure location information using a location module, in some implementations, location information is ascertained by one or more other sensors. For example, in some implementations, the medical device includes a microphone that can measure audio information and correlate the audio information with a particular location.

While we have described a number of examples of how the medical device may enter the various operating modes, other implementations are possible. In some implementations, the medical device may include a microphone, and the medical device may be configured to enter an operating mode based on received audio information. For example, if the medical device detects minimal noise (e.g., below a predetermined threshold) over a particular length of time, it may enter the patient sleep operating mode. In some implementations, one or more other conditions may need to be satisfied for a particular operating mode to be selected. For example, continuing with the previous example, the medical device may enter the sleep operation mode if it detects i) minimal noise, and ii) minimal motion.

While we have described a number of examples of how the treatment sequence can be adjusted based on the operating mode, other implementations are possible. For example, the amount of time afforded to the patient for providing an input to stop the treatment from being delivered may be different than those described above. In some implementations, the amount of time is user-configurable. For example, the amount of time may be set by the patient or another entity (e.g., a caregiver). In some implementations, the amount of time can be determined based on information stored in a database (e.g., a hospital database).

In some implementations, the medical device is configured to interact with one or more other medical devices. While the medical devices described herein have been described as including a variety of sensors, in some implementations, one or more of the sensors may instead be part of a separate medical device. For example, in some implementations, the medical device is configured to interact with a blood pressure monitor, a respiration monitor, a pulse oximeter, and/or a medical device that includes a photoplethysmograph (PPG) sensor. In some implementations, the medical device is configured to interact with a medical device that is configured to detect a heart rate condition in the patient. The medical device for detecting a heart rate condition can provide information to the medical device, and the medical device can select a treatment sequence for correcting the particular heart rate condition (e.g., one or more pacing shocks).

Example Infrastructure

Software running on the medical device controller (e.g., controller 120 of FIGS. 1-3A) can be realized by instructions that upon execution cause one or more processing devices to carry out the processes and functions described above, for example, selecting an operating mode, selecting a treatment sequence, and/or performing a treatment sequence, among others. The instructions can include, for example, interpreted instructions such as script instructions, or executable code, or other instructions stored in a computer readable medium.

A server (e.g., the remote server 326 and 352 as shown in FIGS. 3A and 3B) can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the components of the controller 120 may be contained within a single integrated circuit package. A system of this kind, in which both a processor (e.g., the processor 318) and one or more other components (e.g., the operating condition analyzer 320, the cardiac event detector 324, etc.) are contained within a single integrated circuit package and/or fabricated as a single integrated circuit, is sometimes called a microcontroller. In some implementations, the integrated circuit package includes pins that correspond to input/output ports (e.g., that can be used to communicate signals to and from one or more of the input/output interface devices).

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium (e.g., the data storage 304), for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. In some implementations, operating systems can include a Windows based operating system, OSX, or other operating systems. For instance, in some examples, the processor may be configured to execute a real-time operating system (RTOS), such as RTLinux, or a non-real time operating system, such as BSD or GNU/Linux.

A computer program (also known as a program, software, software application, script, executable logic, or code) can be written in any form of programming language, including compiled or interpreted languages, or declarative or procedural languages, and can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the remote server 326 and 352 as shown in FIGS. 3A and 3B) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the connection between the remote server 326, 352 and the network interface 306 shown in FIGS. 3A and 3B. Examples of communication networks include a local area network ("LAN") and a wide area network ("WAN"), e.g., the Internet.

Having described several aspects of at least one example of this disclosure, the examples of the methods and apparatuses discussed herein are not limited in application to the details of construction and the arrangement of components set forth in this description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples. Accordingly, the foregoing description and drawings are by way of example only Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

What is claimed is:

1. An ambulatory medical device configured for multiple operating modes, comprising:
    a plurality of ECG sensing electrodes for sensing ECG signals of a patient;
    a data storage having stored therein one or more arrhythmia detection parameters;
    at least one processor that is coupled with the plurality of ECG sensing electrodes and that is configured to detect a cardiac arrhythmia condition indicated by the ECG signals based on the one or more arrhythmia detection parameters;
    a plurality of therapy electrodes configured to deliver a treatment to the patient in response to detection of the cardiac arrhythmia condition indicated by the ECG signals; and
    a moisture sensor configured to detect moisture content in an environment of the patient,
    wherein the at least one processor is also coupled with the moisture sensor and the plurality of therapy electrodes, and
    wherein the at least one processor is also configured to
        in a default operating mode, deliver the treatment to the patient based on the one or more arrhythmia detection parameters in response to detection of the cardiac arrhythmia condition,
        change from operating in the default operating mode to operating in a water operating mode based on the detected moisture content transgressing a predetermined threshold value, and
        in the water operating mode, change the one or more arrhythmia detection parameters relative to the default operating mode.

2. The ambulatory medical device of claim 1, wherein the treatment comprises one or both of defibrillation current and a pacing pulse.

3. The ambulatory medical device of claim 1,
    wherein the ambulatory medical device further comprises a wearable medical device, and
    wherein the plurality of therapy electrodes are coupled to the wearable medical device.

4. The ambulatory medical device of claim 1,
    wherein the ambulatory medical device comprises a garment configured to be worn about a torso of the patient, and
    wherein the plurality of ECG sensing electrodes are coupled to the garment.

5. The ambulatory medical device of claim 1, wherein the at least one processor is further configured to:
    in response to detecting the cardiac arrhythmia condition in the default operating mode or in the water operating mode, provide an indication to the patient, via a user interface, that the treatment will be delivered, wherein the indication prompts the patient to provide a response via the user interface;
    in the default operating mode, in response to receiving the response from the patient within a first time period, refrain from delivering the treatment to the patient; and
    in the water operating mode, in response to receiving the response from the patient within a second time period, refrain from delivering the treatment to the patient, the second time period being greater than the first time period.

6. The ambulatory medical device of claim 5,
    wherein the indication is an audible indication,
    wherein, in the default operating mode, the at least one processor is configured to provide the indication at a first volume level, and
    wherein, in the water operating mode, the at least one processor is configured to provide the indication at a second volume level greater than the first volume level.

7. The ambulatory medical device of claim 1,
    wherein the one or more arrhythmia detection parameters includes a sensitivity level used to detect the cardiac arrhythmia condition, and
    wherein to change the one or more arrhythmia detection parameters in the water operating mode, the at least one processor is configured to decrease the sensitivity level.

8. The ambulatory medical device of claim 7, wherein, to decrease the sensitivity level, the at least one processor is configured to increase an amount of time to detect the cardiac arrhythmia condition in the water operating mode relative to a default amount of time to detect the cardiac arrythmia condition in the default operating mode.

9. The ambulatory medical device of claim 7,
wherein the one or more arrhythmia detection parameters includes one or more baseline ECG signals and one or more comparison parameters used to determine a match between the ECG signals sensed by the ECG sensing electrodes and the one or more baseline ECG signals,
wherein to detect the cardiac arrythmia condition the at least one processor is configured to compare the ECG signals sensed by the ECG sensing electrodes with the one or more baseline ECG signals, and
wherein to decrease the sensitivity level, the at least one processor is configured to adjust the one or more comparison parameters.

10. The ambulatory medical device of claim 9,
wherein the one or more comparison parameters include a zero crossing range, and
wherein adjusting the one or more comparison parameters to decrease the sensitivity level includes increasing the zero crossing range relative to a zero crossing range used in the default operating mode.

11. The ambulatory medical device of claim 9,
wherein the one or more comparison parameters include a magnitude threshold, and
wherein adjusting the one or more comparison parameters to decrease the sensitivity level includes increasing a variation range for the magnitude threshold relative to a variation range used in the default operating mode.

12. The ambulatory medical device of claim 7,
wherein the one or more arrhythmia detection parameters includes a threshold ECG score indicative of the cardiac arrhythmia condition, and
wherein to decrease the sensitivity level, the at least one processor is configured to automatically increase the threshold ECG score in the water operating mode.

13. The ambulatory medical device of claim 7, wherein, after the cardiac arrythmia condition has been detected, the at least one processor is configured to apply a noise detector to the ECG signals to confirm detection of the cardiac arrythmia condition.

14. The ambulatory medical device of claim 13,
wherein the at least one processor is configured to perform an analysis of the ECG signals and determine an ECG score based on the analysis of the ECG signals,
wherein, in the default operating mode, the noise detector is configured to confirm the detection of the cardiac arrythmia condition based on the ECG score exceeding a first threshold value, and
wherein, in the water operating mode, the noise detector is configured to confirm the detection of the cardiac arrythmia condition based on the ECG score exceeding a second threshold value greater than the first threshold value.

15. The ambulatory medical device of claim 1, wherein the at least one processor is further configured to automatically change from operating in the water operating mode to operating in the default operating mode based on the detected moisture content falling below the predetermined threshold value.

16. The ambulatory medical device of claim 1, wherein the at least one processor is further configured to automatically change from operating in the water operating mode to operating in the default operating mode after a predetermined amount of time has elapsed.

17. The ambulatory medical device of claim 1, further comprising a user interface configured to receive a manual selection of the default operating mode,
wherein the at least one processor is further configured to change from operating in the water operating mode to operating in the default operating mode based on the manual selection of the default operating mode, and
wherein the manual selection is received via the user interface of the ambulatory medical device.

18. The ambulatory medical device of claim 1, wherein the at least one processor is further configured to:
in response to detecting the cardiac arrhythmia condition in the default operating mode or in the water operating mode, provide an indication to the patient, via a user interface, that the treatment will be delivered, wherein the indication prompts the patient to provide a response via the user interface; and
in response to receiving the response from the patient within a predetermined time period, refrain from delivering the treatment to the patient, wherein the predetermined time period is longer in the water operating mode than in the default operating mode.

19. The ambulatory medical device of claim 1, wherein, in the water operating mode, the at least one processor is further configured to change one or more treatment parameters of the treatment to be delivered by the plurality of therapy electrodes.

20. The ambulatory medical device of claim 19, wherein the one or more treatment parameters include one or more of a number of defibrillation shocks and an energy intensity of the defibrillation shocks.

* * * * *